US006933315B2

(12) United States Patent
Wang et al.

(10) Patent No.: US 6,933,315 B2
(45) Date of Patent: *Aug. 23, 2005

(54) DERIVATIVES OF ISOINDIGO, INDIGO AND INDIRUBIN AND METHODS OF TREATING CANCER

(76) Inventors: Longgui Wang, 4124 161st St., Apt. 1A3, Flushing, NY (US) 11368; Xiaomei Liu, 4124 161st St., Apt. 1A3, Flushing, NY (US) 11358; Ruihuan Chen, 708 Bounty Dr., Suite 801, Foster City, CA (US) 94404

( * ) Notice: Subject to any disclaimer, the term of this patent is extended or adjusted under 35 U.S.C. 154(b) by 0 days.

This patent is subject to a terminal disclaimer.

(21) Appl. No.: 10/864,458

(22) Filed: Jun. 10, 2004

(65) Prior Publication Data

US 2004/0225002 A1 Nov. 11, 2004

Related U.S. Application Data

(63) Continuation of application No. PCT/US02/39866, filed on Dec. 13, 2002, which is a continuation of application No. 10/021,589, filed on Dec. 13, 2001, now Pat. No. 6,566,341.
(60) Provisional application No. 60/407,267, filed on Sep. 3, 2002.

(51) Int. Cl.$^7$ ........................ A61K 31/404; C07D 43/04
(52) U.S. Cl. ........................ 514/414; 514/25; 536/4.1; 536/28.1; 548/457
(58) Field of Search .................... 514/25, 414; 548/457; 536/4.1, 28.1

(56) References Cited

U.S. PATENT DOCUMENTS 5,696,092 A    12/1997   Patierno et al. ................ 514/21

FOREIGN PATENT DOCUMENTS

| WO | WO 99/62503 | * 12/1999 | .......... A61K/31/00 |
| WO | WO 00/61124 | * 10/2000 | .......... A61K/31/00 |
| WO | WO 00/61555 | * 10/2000 | .......... C07D/209/34 |

OTHER PUBLICATIONS

Chunmin Li et al, Bull. Chem. Soc. Jpn., 1996, 69, 1621–1627.*
Alessi, D. R., et al., "PD 098059 is a specific inhibitor of the activation of mitogen–activated protein kinase kinase in vitro and in vivo," *J Biol Chem*, vol. 270, No. 46, pp. 27489–27494 (1995).
Boehrer, S., et al., "In lymphatic cells par–4 sensitizes to apoptosis by down–regulating bcl-2 and promoting disruption of mitochondrial membrane potential and caspase activation," *Cancer Res*, vol. 62, No. 6, pp. 1768–1775 (2002).
Buchdunger, E. et al., "Bcr–Abl inhibition as a modality of CML therapeutic," *Biochim Biophys Acta*, vol. 1551, No. 1, pp. M11–18 (2001).
Buolamwini, J.K., "Cell Cycle Molecular Targets in Novel Anticancer Drug Discovery," *Curr. Pharm. Design*, vol. 6, pp. 379–392 (2000).

Damiens, E. et al., "Anti–mitotic properties of indirubin–3'–monoxime, a CDK/GSK–3 inhibitor: induction of endoreplication following prophase arrest," *Oncogene*, vol. 20, No. 29, pp. 3786–3797 (2001).
DiPaola, R.S. et al., "Clinical and biologic activity of an estrogenic herbal combination (PC–SPES) in prostate cancer," *N Engl J Med*, vol. 339, No., 12, pp. 785–791 (1998).
Druker, B.J. et al., "Activity of a specific inhibitor of the BCR–ABL tyrosine kinase in the blast crisis of chronic myeloid leukemia and acute lymphoblastic leukemia with the Philadelphia chromosome," *N Engl J Med*, vol. 344, No. 14, pp. 1038–1042 (2001).
Freitas, J.J. et al., "Walker–256 tumor growth causes oxidative stress in rat brain," *J Neurochem*, vol. 77, No. 2, pp. 655–663 (2001).
Frey, R. S. et al., "Effects of genistein on cell proliferation and cell cycle arrest in nonneoplastic human mammary epithelial cells: involvement of Cdc2, p21](waf/cip1), p27(kip1), and Cdc25C expression," *Biochem Pharmacol*, vol. 61, No. 8, pp. 979–989 (2001).
Furukawa, Y., "Cell cycle control genes and hematopoietic cell differentiation," *Leuk Lymphoma*, vol. 43, No. 2, pp. 225–231 (2002).
Gianni, L. et al., "Nonlinear pharmacokinetics and metabolism of paclitaxel and its pharmacokinetic/pharmacodynamic relationships in humans," *J Clin Oncol*, vol. 13, No. 1, pp. 180–190 (1995).
Gray, N. et al., "ATP–site Directed Inhibitors of Cyclin–dependent Kinases," *Curr. Medicinal Chem.*, vol. 6, No. 9, pp. 859–875 (1999).
Han, J., "Traditional Chinese medicine and the search for new antineoplastic drugs,". *J Ethnopharmacol*, vol. 24, No. 1, pp. 1–17 (1988).
Hoessel, R. et al., "Indirubin, the active constituent of a Chinese Antileukaemia medicine, inhibits cyclin–dependent kinases," Macmillan Magazines Ltd., Nature Cell Biology, vol. 1, pp. 60–67 (1999).

(Continued)

*Primary Examiner*—James O. Wilson
*Assistant Examiner*—Ganapathy Krishnan

(57) ABSTRACT

A compound called NATURA, which is a derivative of Isoindigo is useful in aiding the general health of a patient and specifically is beneficial in preventing or treating cancer. This compound and other related Isoindigo, Indigo and Indirubin derivatives are designed such that the bioactivity or bioavailability of the compound is increased. Methods of synthesizing these derivatives is also taught. In addition, pharmaceutical compositions that include a therapeutically effective amount of at least one of these derivatives and a pharmaceutically acceptable carrier. A method for the use of these pharmaceutical compositions and compounds is taught, wherein a therapeutically effective amount is administered to an animal having solid tumor cancer. The pharmaceutical composition or compound can be re-administered to the animal until a desired treatment or result is accomplished.

15 Claims, 13 Drawing Sheets

OTHER PUBLICATIONS

Huizing, M.T. et al., "Pharmacokinetics of paclitaxel and metabolites in a randomized comparative study in platinum–pretreated ovarian cancer patients," *J Clin Oncol*, vol. 11, No. 11, pp. 2127–2135 (1993).

Ji, X.J. et al., "Pharmacological studies of meisoindigo: absorption and mechanism of action," *Biomed Environ Sci*, vol. 4, No. 3, pp. 332–337 (1991).

Kong, M., et al., "Cyclin F regulates the nuclear localization of cyclin B1 through a cyclin–cyclin interaction," *Embo J*, vol. 19, No. 6, pp. 1378–1388 (2000).

Kreis, W. et al., "Unique synergism or antagonism of combinations of chemotherapeutic and hormonal agents in human prostate cancer cell lines," *Br J Urol*, vol. 79, No. 2, pp. 196–202 (1997).

Kunikata, T. et al., "Indirubin inhibits inflammatory reactions in delayed–type hypersensitivity," *Eur J Pharmacol*, vol. 410, No. 1, pp. 93–100 (2000).

Leclerc et al., "Indirubins Inhibit Glycogen Synthase Kinase–3β and DCK5/P25, Two Protein Kinases Involved in Abnormal Tau Phosphorylation in Alzheimer's Disease", *J. Biol. Chem.*, vol. 276, No. 1, pp. 251–260 (2001).

Li, C. et al., "The Synthesis, Antileukemic Activity, and Crystal Structures of Indirubin Derivatives," *Bull. Chem. Soc. Jpn.*, vol. 69, pp. 1621–1627 (1996).

Li, X.K. et al., "Huanglian, A chinese herbal extract, inhibits cell growth by suppressing the expression of cyclin B1 and inhibiting CDC2 kinase activity in human cancer cells," *Mol Pharmacol*, vol. 58, No. 6, pp. 1287–1293 (2000).

Liu, X.M. et al., "Induction of differentiation and down–regulation of c–myb gene expression in ML–1 human myeloblastic leukemia cells by the clinically effective anti–leukemia agent meisoindigo," *Biochem Pharmacol*, vol. 51, No. 11, pp. 1545–1551 (1996).

Marko, D. et al., "Inhibition of cyclin–dependent kinase 1 (CDK1) by indirubin derivatives in human tumour cells," *Br J Cancer*, vol. 84, No. 2, pp. 283–289 (2001).

Merck Manual of Diagnosis and Therapy, 15th Edition, pp. 1218–1219 (1987).

Mitani, N. et al., "Inhibitory effect of berberine on the mediastinal lymph node metastasis produced by orthotopic implantation of Lewis lung carcinoma," *Cancer Lett*, vol. 165, No. 1, pp. 35–42 (2001).

Morgan, D.O., "Principles of CDK regulation," *Nature*, vol. 374, No. 6518, pp. 131–134 (1995).

Ohtsu, T. et al., "Clinical pharmacokinetics and pharmacodynamics of paclitaxel: a 3–hour infusion versus a 24–hour infusion," *Clin Cancer Res*, vol. 1, No. 6, pp. 599–606 (1995).

Senderowicz, A.M., "Development of cyclin–dependent kinase modulators as novel therapeutic approaches for hematological malignancies," *Leukemia*, vol. 15, No. 1, pp. 1–9 (2001).

Sharifi, N. et al., "Targeted chemotherapy: chronic myelogenous leukemia as a model," *J Mol Med*, vol. 80, No. 4, pp. 219–232 (2002).

Steinman, R. A., "Cell cycle regulators and hematopoiesis," *Oncogene*, vol. 21, No. 21, pp. 3403–3413 (2002).

Wang, L.G., et al., "Activation on casein kinase II in ML–1 human myeloblastic leukemia cells requires IGF–1 and transferrin," *J Leukoc Biol*, vol. 57, No. 2, pp. 332–334 (1995).

Wang, L.G., et al., "Down–regulation of prostate–specific antigen expression by finasteride through inhibition of complex formation between androgen receptor and steroid receptor–binding consensus in the promoter of the PSA gene in LNCaP cells," *Cancer Res*, vol. 57, No. 4, pp. 714–719 (1997).

Wicki, A. et al., "The Rho/Rho–kinase and the phosphatidylinositol 3–kinase pathways are essential for spontaneous locomotion of Walker 256 carcinosarcoma cells," *Int J Cancer*, vol. 91, No. 6, pp. 763–771 (2001).

Wu–Wong, J. R., et al., "Identification and characterization of A–105972, an antineoplastic agent," *Cancer Res*, vol. 61, No. 4, pp. 1486–1492 (2001).

Yamaura, T., et al., "Model for mediastinal lymph node metastasis produced by orthotopic intrapulmonary implantation of lung cancer cells in mice," *Hum Cell*, vol. 12, No. 4, pp. 197–204 (1999).

\* cited by examiner

Indirubin

Meisoindigo

Natura

A: Induction of DNA Fragmentation in LNCaP Prostate Cancer

B: Induction of DNA Fragmentation in N2A Neuroblastoma Cells

LNCaP Cell Exposure to Natura-β at concentration of

A: By SDS-gel

B: By SDS-gel

A': By density

B': By density

Panel A: Cdk2        Panel B: Cdk4

A: By SDS-PAGE

B: By scintillation

DERIVATIVES OF ISOINDIGO, INDIGO AND INDIRUBIN AND METHODS OF TREATING CANCER

This application is a continuation of PCT/US02/39866 filed Dec. 13, 2002 which is a continuation of application Ser. No. 10/021,589 filed Dec. 13, 2001 now U.S. Pat. No. 6,566,341 and claims benefit of application Ser. No. 60/407,267 filed Sep. 3, 2002.

TECHNICAL FIELD

The invention relates to new and useful compounds that are derivatives of isoindigo, indigo and indirubin and their use in treating solid tumor cancer in a subject. The invention further relates to methods of synthesizing the useful derivatives.

BACKGROUND

Prevention and treatment of cancer has significantly improved in the United States during the past decade because of advancements in epidemiology, the technology of treatment, and the ability to deliver earlier diagnosis. Finding a cure for a diversity of cancers, such as lung, breast, prostate, colon and others however, is still a major challenge. Current approaches for the treatment of cancers are, however, still limited to the lengthening of life, or the increase in the quality of life. Additionally, most meaningful therapeutics still have significant side effects. Therefore, it is imperative to find more effective therapeutic agents with lower side effects.

Tumor cells are characterized by uncontrolled cell proliferation due to the loss of the integration and coordination of extracellular signals with the cell cycle machinery. A typical cell cycle is classified into G1, S, G2 and M phases [1–3] and is illustrated in FIG. 2. In mammalian cells, proliferation is controlled in the G1 phase of the cell cycle. At the restriction point, cells can have different destinies. Examples of these cell destinies include: 1) leaving the cell cycle and entering a reversible quiescence phase; 2) exiting cell cycle and undergoing apoptosis; 3) differentiating and irreversibly exiting from the cell cycle; and 4) passing through the restriction point and becoming largely independent of extracellular signals and progress automatically through subsequent cell cycle phases (S, G2, M) to the next G1 phase. A variety of proteins are in turn responsible for the regulated progression of cells through the cell cycle. The key components of cell cycle machinery are the cyclins, the cyclin-dependent kinases (CDKs) and their inhibitors. Cyclins are a remarkably diverse family of proteins, which are synthesized from the mid/late of G1 phase till the M phase of the cell cycle and then rapidly degraded. A CDK typically contains a catalytic domain of 300 amino acids, which is inactive by it self. Cdks become active by binding to a cyclin. Activity of cdks is inhibited by their endogenous inhibitors (cdk inhibitors, or cdkIs include p15/p16/p18/p19 and p21/p27). Specific cyclin/CDK complexes are formed at specific stages of the cell cycle and their activities are required for progression of the cell cycle through S phase and mitosis.

Over-activation of CDKs is a character of a majority of human tumor cells. Strategies have been developed to modulate CDK activity for therapeutic intervention by either directly targeting the catalytic CDK subunit or indirectly affecting the CDK regulatory pathways [3]. Small molecule CDK inhibitors were designed to interact specifically with the ATP binding site of CDKs, such as flavopiridol congeners, polysulfates, toyocamycin derivatives, etc. Anticancer effects have been shown in clinical trials for those agents. Modulation of CDK activities can be achieved by regulating phosphorylation of CDKs or altering the expression of the CDKs or the their inhibitors (CKDIs). It is difficult to find specific modulators that do not interfere with other cell cycle components and do not affect normal cells.

A need thus exists for compounds that are easily produced and are highly effective at treating cancer but have minimal toxicity to normal cells.

Many Chinese herbs contain potent anti-cancer chemical components. For example, several Chinese plants such as *Camptotheca acuminata* (camptothecin), *Cephalotaxus* sp. (homoharringtonine/harringtonine) have provided compounds with significant antitumor activity [6]. PC-SPES, a mixture consisting of extracts from eight herbs for the treatment of prostate cancer, has been demonstrated to have potent anti-androgen activity [7]. Huanglian, a Chinese herbal extract, has recently been shown to inhibit cell growth by suppressing the expression of cyclin B1 and inhibiting CDC2 kinase activity in human cancer cells [8]. In addition, many Chinese herbal products have demonstrated an important role in cancer chemoprevention.

Studies have recently demonstrated that indirubin molecules from the anticancer Chinese herb—Qing Dai, exhibit their anticancer activity through modulating cyclin-dependent kinases [9].

Our previous studies demonstrated that meisoindigo, a second generation of indirubins, arrests leukemia cells at $G_1$ phase, inhibits expression of oncogene c-myb, and induces cell differentiation and maturation at low concentrations (low toxicity) in which cell growth is completely inhibited without a decrease in cell viability [10, 11]. Recent studies demonstrate that indirubin selectively inhibits cyclin-dependent kinases (cdks) by competing with ATP for binding to the catalytic site of the kinase (FIG. 2) [12].

SUMMARY OF THE INVENTION

The present invention provides novel derivatives of isoindigo, indigo and indirubin that can be used to treat cancer in animals. These novel compounds exhibit minimal toxicity and side effect with a substantial chemotherapeutic index. These compounds allow for the treatment of a variety of cancers with minimal side affects experienced by the patient. Furthermore, the novel compounds are simple, stable chemical molecules that are substantially easy to produce and administer.

One of the advantages of the present invention is that the novel compounds have an increased solubility and bioavailability compared to the prior art molecules and thus are better suited for the treatment of cancer.

The present invention is directed to a specific group of novel compounds that are derivatives of isoindigo, indigo and indirubin as shown in formulas (I), (II) and (III) respectively

FORMULA (I)

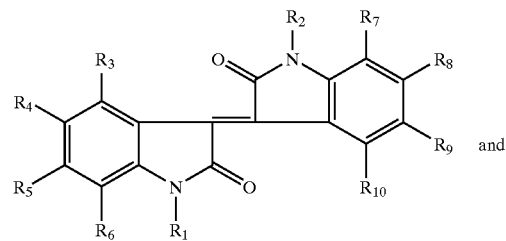

and

-continued

FORMULA II

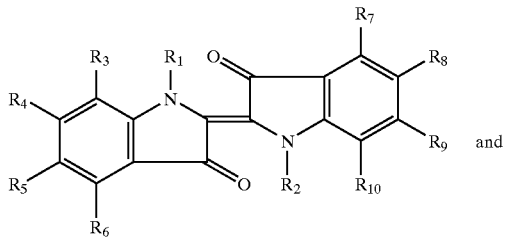

and

FORMULA (III)

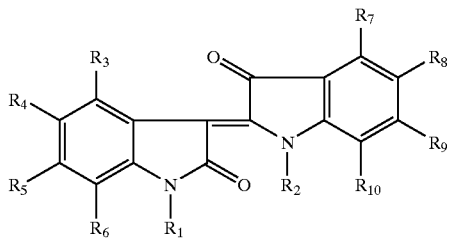

wherein $R_1$, $R_2$, $R_3$, $R_4$, $R_5$, $R_6$, $R_7$, $R_8$, $R_9$, or $R_{10}$ is independently a hydrogen, a monosaccharide, a disaccharide, a halogen, a hydrocarbyl group, or a functional hydrocarbyl group unsubstituted or substituted with one or more hydroxy moieties, carboxy moieties, nitroxy moieties, monosaccharides, disaccharides, amines, amides, thiols, sulfate, sulfonate, sulfonamide or halogens, wherein the hydrocarbyl has 1 to 12 carbon atoms.

A preferred embodiment is one in which $R_1$ or $R_2$ is a monosaccharide and typically it is preferred that the monosaccharide be acetylated.

A particularly preferred embodiment of the invention, referred to herein as NATURA, is the compound of the following Formula (IV)

FORMULA (IV)

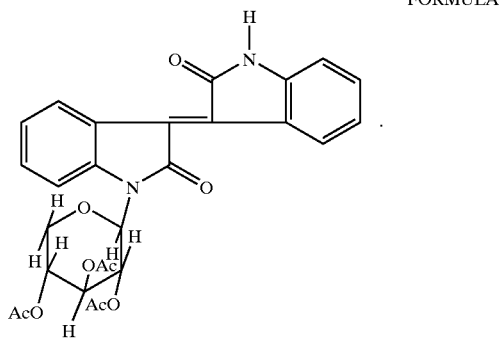

The present invention further provides a method of treating solid tumor cancer and leukemia comprising administering to the animal a therapeutically effective amount of the novel derivatives of indigo, isoindigo and indirubin provided by the invention. Preferably the compound administered has the chemical structure of Formula (IV) or

FORMULA (V)

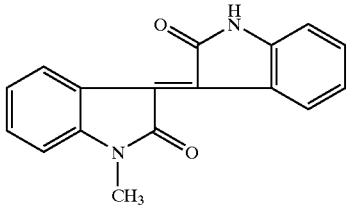

Generally, the solid tumor cancer being treated is colon cancer, hormone dependent or independent prostate cancer, breast cancer, or lung cancer. Preferably the solid tumor cancer is hormone dependent or independent prostate cancer.

Advantageously, the compound can be administered in combination with additional therapeutic agents. Typically, these agents include radiotherapeutic agents, hormonal therapy agents, immunotherapeutic agents, chemotherapeutic agents, cryotherapeutic agents or gene therapy agents. Preferably, at least one of the agents known as Casodex or Proscar is administered in combination with the compound for optimum results.

Additionally, the present invention provides a method of synthesizing a meisoindigo compound by adding about equal molar amounts of 2-hydroxyindole and N-methyl-indolinyl-diketone to produce a reaction substance; mixing the reaction substance with an excess amount of glacial acetic acid (i.e., about 2.0 L of glacial acetic acid for about 1 molar of reaction substance) to make a mixture; heating the mixture to about 70 to 80° C. for 1 to 3 hours to form a precipitate, and recovering the precipitate as the meisoindigo compound.

It is preferable that the precipitate is washed with at least glacial acetic acid, water, or ethanol.

The present invention also provides pharmaceutical compounding that can be used to treat cancer or illnesses in an animal, comprising a therapeutically effective amount of a compound of the invention and a pharmaceutically acceptable carrier.

DETAILED DESCRIPTION OF THE PREFERRED EMBODIMENTS

Figure 1:
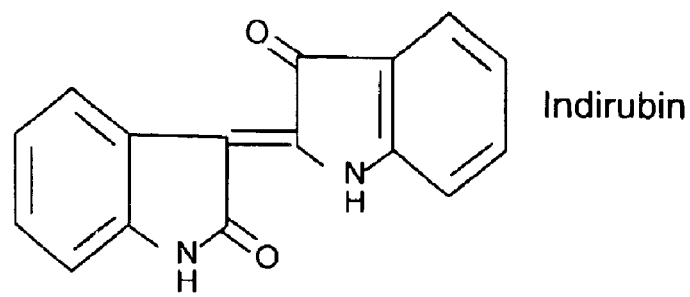
FIG. 1 shows the chemical structures of Indirubin, Meisoindigo, and NATURA, a new chemical entity in accordance with the invention.
Figure 1:
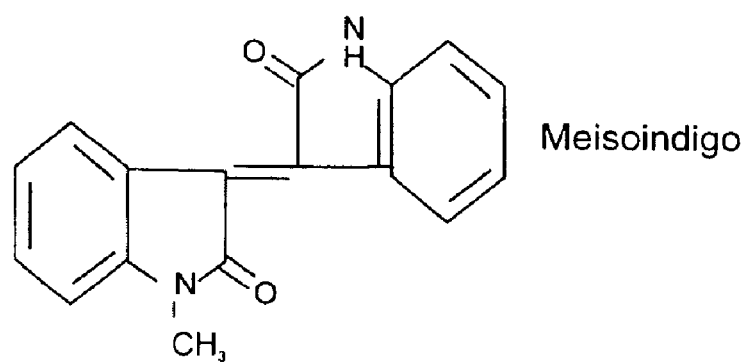
Figure 1:
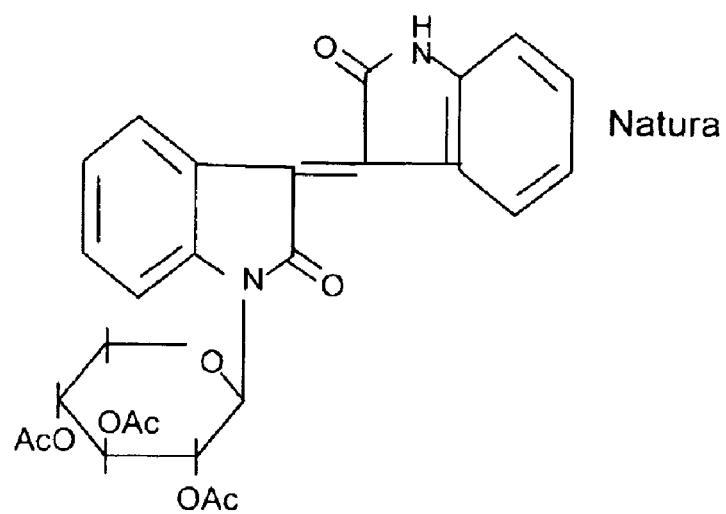

The present invention is directed to derivatives of isoindigo, indigo and indirubin that can be used to treat cancer and other illnesses in an animal and also can be used to inhibit activities, which is useful in treating other human disorders, such as Alzheimer's disease, psoriasis, cardiovascular diseases, glomerulonephritis. The examples given below are simply to demonstrate different embodiments of the invention and are not intended in any way to limit the scope of the present invention thereto.

The present invention is directed to a specific group of compounds that are derivatives of isoindigo, indigo, and indirubin as shown in formulas (I), (II), and (III) respectively.

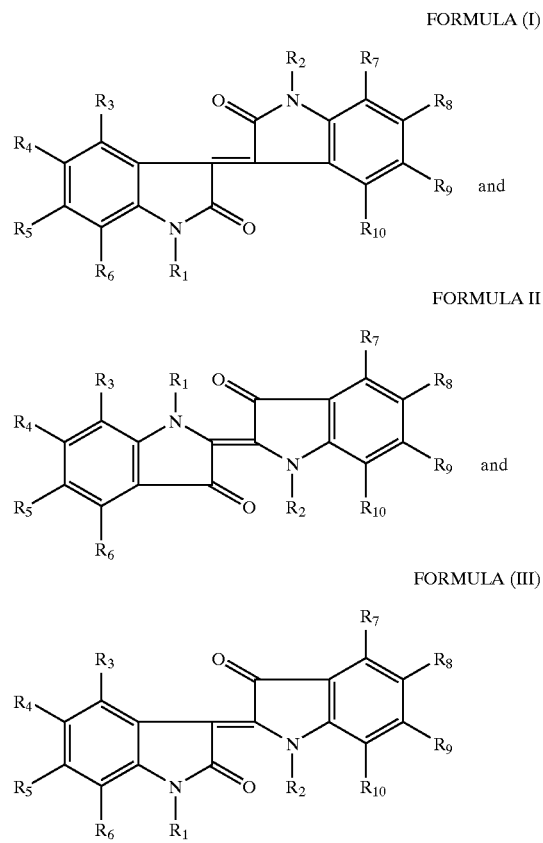

FORMULA (I)

FORMULA II

FORMULA (III)

wherein $R_1$, $R_2$, $R_3$, $R_4$, $R_5$, $R_6$, $R_7$, $R_8$, $R_9$, or $R_{10}$ is independently a hydrogen, a monosaccharide, a disaccharide, a halogen, a hydrocarbyl group, or a functional hydrocarbyl group unsubstituted or substituted with one or more hydroxy moieties, carboxy moieties, nitroxy moieties, monosaccharides, disaccharides, amines, amides, thiols, sulfate, sulfonate, sulfonamide or halogens, wherein the hydrocarbyl has 1 to 12 carbon atoms.

Preferred compounds are those in which at least one $R_1$, $R_2$, $R_3$, $R_4$, $R_5$, $R_6$, $R_7$, $R_8$, $R_9$, or $R_{10}$ is independently a monosaccharide, a disaccharide, or a hydrocarbyl group or a functional hydrocarbyl group substituted with one or more hydroxy moieties, carboxy moieties, nitroxy moieties, monosaccharides, disaccharides, amines, amides, thiols, or halogens, wherein the hydrocarbyl has 1 to 8 carbon atoms; and at least one of $R_1$, $R_2$, $R_3$, $R_4$, $R_5$, $R_6$, $R_7$, $R_8$, $R_9$, or $R_{10}$ enhances the bioactivity or bioavailability of the compound. For example, by mimicking the ribose group of ATP, thus increasing the compounds bioactivity.

It is preferable that $R_1$, $R_2$, $R_3$, $R_4$, $R_5$, $R_6$, $R_7$, $R_8$, $R_9$, or $R_{10}$ enhances the bioactivity or bioavailability of the compound by more closely mimicking the structure of ATP or by increasing the solubility of the compound. It is more preferable that both the bioactivity and bioavailability are increased by one or more of $R_1$, $R_2$, $R_3$, $R_4$, $R_5$, $R_6$, $R_7$, $R_8$, $R_9$, or $R_{10}$.

Additional preferred compounds are those in which $R_1$ or $R_2$, is a monosaccharide, a disaccharide, or a hydrocarbyl group or a functional hydrocarbyl group substituted with one or more hydroxy moieties, carboxy moieties, nitroxy moieties, monosaccharides, disaccharides, amines, amides, thiols, sulfate, sulfonate, sulfonamide, or halogens, and preferably where the hydrocarbyl has 1 to 8 carbon atoms and the functional hydrocarbyl has 1 to 8 carbon atoms and one hydroxyl group for each two carbon atoms. In many cases only one of $R_1$ or $R_2$ needs to be one of the recited moieties, with one of the preferred substituents being —$CH_2CH_2OH$.

It is preferable that the monosaccharide or disaccharide be acetylated. Preferred compounds of Formulas (I), (II), and (III) are ones in which $R_1$ or $R_2$ is an acetylated monosaccharide. The acetylated monosaccharide $R_1$ or $R_2$ can be any monosaccharide, but preferably is acetylated glucose, fructose, ribulose, galactose, mannose, cellobiose, allose, altrose, ribose, xylose, or arabinose, and more preferably acetylated xylose, glucose, arabinose, mannose or ribose. Preferably the monosaccharide has 1 to 8 acetyl groups, more preferably 2 to 4 acetyl groups.

One of the most preferred compounds of the invention is NATURA, having the chemical structure as set forth in Formula (IV).

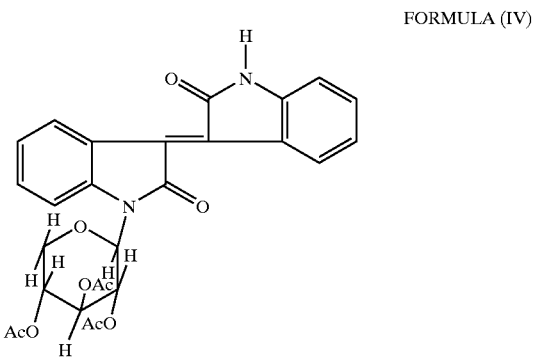

FORMULA (IV)

Other highly preferred compounds of the invention are NATURA derivatives, wherein the acetylated xylose molecule is substituted for a different acetylated monosaccharide preferably, acetylated glucose, ribose, mannose, or arabinose. In Example 6 below, the inventors provide results of the increased activity of NATURA and its derivatives. Based on the results, it appears that the acetylation of the monosaccharide greatly increases the activity of NATURA, and its derivatives, by increasing its bioavailability. Derivatives of NATURA having unacetylated sugar groups showed a much weaker activity against LNCaP cells compared to the acetylated derivatives. One factor in determining the bio-avaliability of a molecule is whether or not it can pass through cell membrane. Diffusion through cell membranes is determined by the ratio of oil/water (o/w). If polarity is too high (water soluble) or too low (oil soluble), the molecule will have increased difficulty in passing through the membrane by simple diffusion. NATURA and the acetylated NATURA derivatives have a reduced polarity compared to the nonacetylated derivatives, which increases their membrane diffusion capabilities and bioavailability.

Surprisingly the compounds of the invention, in particular NATURA and its derivatives, have been found to be highly effective in treating solid tumor cancers such as colon cancer, hormone dependent or independent prostate cancer, breast cancer, or lung cancer. Preferably the solid tumor cancer being treated is hormone dependent or independent prostate cancer.

Preferably the compound administered to the animal having a solid tumor cancer is of the chemical structure of Formula (IV) or

FORMULA (V)

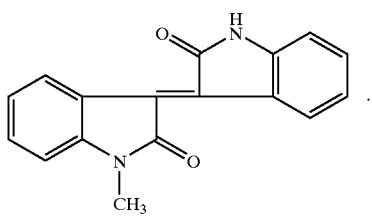

The following lists are not intended to be all encompassing, but simply demonstrative. The term "hydrocarbyl" in the context of the present invention, and in the above formulas, broadly refers to a monovalent hydrocarbon group in which the valency is derived by abstraction of a hydrogen from a carbon atom. Hydrocarbyl includes, for example, aliphatics (straight and branched chain), cycloaliphatics, aromatics and mixed character groups (e.g., aralkyl and alkaryl). Hydrocarbyl also includes such groups with internal unsaturation and activated unsaturation. More specifically, hydrocarbyl includes (but is not limited to) such groups as alkyl, cycloalkyl, aryl, aralkyl, alkaryl, alkenyl, cycloalkenyl and alkynyl, preferably having up to 12 carbon atoms. The preferred embodiments include those in which the hydrobcarbyl group has 1 to 8 carbon atoms. These and other hydrocarbyl groups may optionally contain a carbonyl group or groups (which is/are included in the carbon count) and/or a heteroatom or heteroatoms (such as at least one oxygen, sulfur, nitrogen or silicon), in the chain or ring.

The term "functional hydrocarbyl" in the context of the present invention, and in the above formulas, broadly refers to a hydrocarbyl possessing pendant and/or terminal "reactive" and/or "latent reactive" functionality and/or leaving groups. Reactive functionality refers to functionality that is reactive with common monomer/polymer functionality under normal conditions well understood by those persons of ordinary skill in the relevant art. As examples of reactive functionality may be mentioned active hydrogen containing groups such as hydroxyl, amino, carboxyl, thio, amido, carbamoyl and activated methylene; isocyanato; cyano; epoxy; ethylenically unsaturated groups such as allyl and methallyl; and activated unsaturated groups such acryloyl and methacryloyl, and maleate and maleimido (including the Diels-Alder adducts thereof with dienes such as butadiene).

Latent reactive functionality within the meaning of the present invention and, as would clearly be understood by those persons of ordinary skill in the relevant art, refers to reactive functionality which is blocked or masked to prevent premature reaction. As examples of latent reactive functionality may be mentioned ketimines and aldimines (amines blocked, respectively, with ketones and aldehydes); amine-carboxylate salts; and blocked isocyanates such as alcohol (carbamates), oxime and caprolactam blocked variations. A "leaving" group within the meaning of the present invention and, as would clearly be understood by those persons of ordinary skill in the relevant art, is a substituent attached to the hydrocarbyl chain or ring which during reaction is displaced to create a valency on a carbon or hetero atom in the hydrocarbyl chain or ring. As examples of leaving groups may be mentioned, halogen atoms such as chlorine, bromine and iodine; quaternary ammonium salts; sulfonium salts; and sulfonates.

A monosaccharide or disaccharide of the present invention is preferably glucose, fructose, ribulose, galactose, mannose, cellobiose, allose, altrose, ribose, xylose, arabinose, sucrose, or lactose. Preferably D-glucose, D-ribose, D-glacatose, D-lactose or D-sucrose is used. Advantageously the monosaccharide or disaccharide is acetylated.

The term "halogen" indicates fluorine, chlorine, bromine, or iodine. A preferred halogen is fluorine or chlorine.

As used herein, amino acid means an L- or D-amino acid (or a residue thereof), preferably L-, selected from the group consisting of alanine, arginine, asparagines, aspartic acid, cysteine, glutamine, glutamic acid, glycine, histidine, isoleucine, leucine, lysine, methionine, phenylalanine, proline, serine, threonine, tryptophan, tyrosine, or valine. The term peptide is two or more amino acids joined by a peptide bond, preferably containing 2 to 8 amino acids, and more preferably containing 2 to 6 amino acids.

The present invention also provides a therapeutic method for treating an animal with cancer comprising administering to an animal a therapeutically effective of the compounds described above. The invention may also be used to prevent cancer. The compounds disclosed herein play a role in chemoprevention. The compounds can be used to prevent cancer by acting as cdk inhibitors, that block cancer from progressing (second step in the carcinogenesis), thus preventing its occurrence.

The invention may be used to an animal with cancer, wherein it is preferable that the animal is a mammal and more preferable that the animal is human. Furthermore, it is believed that the invention can be used to treat any type of cancer, and data is provided herein to demonstrate effectiveness for colon cancer, hormone dependent and independent prostate cancer, breast cancer, and leukemia. It is preferable, however, that the cancer being treated is a solid tumor cancer.

It should also be noted that therapeutic benefits may be realized by the administration of at least two, three or more of the compounds concurrently or sequentially. The compounds may also be combined with other therapies to provide combined therapeutically effective amounts. The compound can be administered, for example, in combination with additional agents selected from the group consisting of radiotherapeutic agents, hormonal therapy agents, immunotherapeutic agents, chemotherapeutic agents, cryotherapeutic agents and gene therapy agents. Preferably, Casodex or Proscar is administered in combination with the compound.

Additionally, the present invention provides a method of synthesizing meisoindigo comprising: adding about equal molar amounts of 2-hydroxyindole and N-methyl-indolinyl-diketone to produce a reaction substance; mixing the reaction substance with about 2.0 L of glacial acetic acid for about 1 molar of reaction substance to make a mixture; and heating the mixture to about 70 to 80° C. for 1 to 3 hours to form a precipitate.

It is preferable that the precipitate is washed with at least glacial acetic acid, water, or ethanol.

The present invention further provides a pharmaceutical composition for treating cancer in an animal comprising a therapeutically effective amount of a derivative of isoindigo or indirubin or combination of derivatives and a pharmaceutically acceptable carrier. This can take a variety of forms adapted to the chosen route of administration as discussed above.

Those skilled in the art will recognize various synthetic methodologies that may be employed to prepare non-toxic pharmaceutically acceptable compositions of the compounds encompassed by Formulas I, II and III. Those skilled in the art will recognize a wide variety of non-toxic pharmaceutically acceptable solvents that may be used to prepare solvates of the compounds of the invention, such as water, ethanol, mineral oil, vegetable oil, and dimethylsulfoxide.

The compounds of general Formulas I, II and III may be administered orally, topically, parenterally, by inhalation or spray or rectally in dosage unit formulations containing conventional non-toxic pharmaceutically acceptable carriers, adjuvants and vehicles. It is further understood that the best method of administration may be a combination of methods. Oral administration in the form of a pill, capsule, elixir, syrup, lozenge, troche, or the like is particularly preferred. The term parenteral as used herein includes subcutaneous injections, intradermal, intravascular (e.g., intravenous), intramuscular, spinal, intrathecal injection or like injection or infusion techniques. In addition, there is provided a pharmaceutical formulation comprising a compound of general Formulas I, II and III and a pharmaceutically acceptable carrier. One or more compounds of general Formulas I, II and III may be present in association with one or more non-toxic pharmaceutically acceptable carriers and/or diluents and/or adjuvants and if desired other active ingredients. The pharmaceutical compositions containing compounds of general Formulas I, II and III may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example *arachis* oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or *arachis* oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of general Formulas I, II and III may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials are cocoa butter and polyethylene glycols.

Compounds of general Formulas I, II and III may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

For administration to non-human animals, the compound or a composition containing the compound may be added to the animal's feed or drinking water. Also, it will be convenient to formulate animal feed and drinking water products so that the animal takes in an appropriate quantity of the compound in its diet. It will further be convenient to present the compound in a composition as a premix for addition to the feed or drinking water.

Dosage levels of the order of from about 0.01 mg to about 140 mg per kilogram of body weight per day are useful in the treatment of the above-indicated conditions (about 0.5 mg to about 7 g per patient per day). It is preferable, however, that the dosage amount be about 10 mg to 500 mg per day when administering to a human. The amount of active ingredient that may be combined with the carrier materials to produce a single dosage form will vary depending upon the host treated and the particular mode of administration. Dosage unit forms will generally contain between from about 1 mg to about 500 mg of an active ingredient.

Frequency of dosage may also vary depending on the compound used and the particular disease treated. However, for treatment of most disorders, a dosage regimen of 4 times daily or less is preferred. It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

Preferred compounds of the invention will have desirable pharmacological properties that include, but are not limited to, oral bioavailability, low toxicity, low serum protein binding and desirable in vitro and in vivo half-lifes. Penetration of the blood brain barrier for compounds used to treat CNS disorders is necessary, while low brain levels of compounds used to treat peripheral disorders are often preferred.

Assays may be used to predict these desirable pharmacological properties. Assays used to predict bioavailability include transport across human intestinal cell monolayers, including Caco-2 cell monolayers. Toxicity to cultured hepatocyctes may be used to predict compound toxicity. Penetration of the blood brain barrier of a compound in humans may be predicted from the brain levels laboratory animals that receive the compound intravenously.

Serum protein binding may be predicted from albumin binding assays. Such assays are described in a review by Oravcova, et al. (Journal of Chromatography B (1996) volume 677, pages 1–27).

Compound half-life is inversely proportional to the frequency of dosage of a compound. In vitro half-lives of compounds may be predicted from assays of microsomal half-life as described by Kuhnz and Gieschen (Drug Metabolism and Disposition, (1998) volume 26, pages 1120–1127).

It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

The amount of the composition required for use in treatment will vary not only with the particular compound selected but also with the route of administration, the nature of the condition being treated and the age and condition of the patient and will be ultimately at the discretion of the attendant physician or clinician.

EXAMPLES

Examples of the compounds of Formulas I–V and their uses to treat cancer are described in the following Examples.

A number of indirubin derivatives were designed and screened for their Anti-cancer activities. Among the derivatives screened, 1-(β-D-O-Triacetyl-xylopyranosyl)-isoindigo, with chemical formula $C_{27}H_{24}N_2O_9$ (NATURA, see chemical structure in FIG. 1) has been found to be the most active against not only leukemia, but also various human cancer cells with lower toxicity effects.

Reagents: Meisoindigo and NATURA and other sugar derivatives were synthesized by Natrogen, purified by PHLC with a purity of 98.5%, and structures verified by spectrum of Mass, Infrared, and nuclear magnetic resonance. NATURA is a reddish crystal powder, no smell, and tasteless. It is soluble in dimethyl sulfoxide (DMSO), and slightly dissolves in ethanol, acetone, chloroform, and rarely dissolves in water. Retinoid Acid, daunomycin, paclitaxel were obtained from Sigma Chemical Company (St. Louis, Mo.), Casodex and Proscar were from commercial pills and equivalent amount was calculated according to their labels. Antibodies against cdk2 (cdc-2), cdk4/6, PKC, ERK2 and secondary antibodies for Western blot were purchased from Santa Cruz Biotechnology Inc., and antibody against cyclin D1 from DAKO. Protein Agarose A+G was provided by Oncogene. $\gamma$-[$^{32}$P]-ATP was purchased from PerkinElmer Scientific Inc. Western blot detection kit was provided by Amersham. Reagents for SDS-PAGE and DNA agarose electrophoresis were purchased from Bio-Rad, Inc., and other chemicals were purchased from Sigma.

Cell Cultures: Human cancer cell lines of breast (MCF-7 and SKBR-3), colon (LOVO and DLD-1), prostate (LNCaP, DU 145 and PC-3), neuroblastoma, (N2A) and human epithelial cell line HUVEC were purchased from American Type Culture Collection (Rockville, Md.). The cells were maintained according to manufacture's instructions.

Anticancer activity against Walker 256: Wistar rats with body weights between 50 to 55 grams, were randomly divided into several groups, ten of each, respectively. Approximately $2 \times 10^6$ of the Walker sarcoma cells were transplanted into a Wistar rat. Twenty-four hours after the transplantation, equal molar dosage (0.384 mM/kg) of NATURA or other sugar derivatives were given orally for 10 days. The animals in the control group were given 0.1 ml saline (drug vehicle, negative control) for the same periods of time as treated group. Twenty-four hours after the last administration, the animals were sacrificed and tumors were removed and weighed.

Assay for cyclin dependent kinase activity: HUVEC and LNCaP cells were cultured in EMB (endothelial cell basal medium) and RPMI 1640 containing 10% FBS, respectively. The cells grown exponentially were exposed to indicated concentrations of meisoindigo or NATURA for 24 hr. The cells were harvested, washed, and total proteins extracted as described previously [13]. One hundred $\mu$g of the proteins were immuno-precipitated using antibodies against cdk2, cdk4/6, PKC, ERK2 or cyclin D1 overnight at 4° C. in the presence of a cocktail of protease inhibitors. The immuno-precipitates were washed 4 times with protein extraction buffer and once with kinase assay buffer, and reacted with 75 $\mu$g/ml histone H1 in the presence of $[\gamma\text{-}^{32}P]$-ATP (2.5 $\mu$Ci/10 $\mu$M). The phosphorylated histone H1 (represent cdk activity) was measured by scintillation counting or by SDS-polyacrylaimde gel electrophoresis [14, 15]. The direct inhibitory effects of Meisoindigo and NATURA were also measured by reaction of immuno-purified specific enzyme from untreated cells directly with the Meisoindigo or NATURA.

It was observed that this agent strongly inhibits cyclin D mediated CDK activities and cell growth of various types of human cancer cells including cancer cell lines of breast, prostate, colon and lung ($IC_{50}$ are between 1.5 to 9.0 $\mu$M). Both Meisoindigo and NATURA also exhibit very low toxicity with $LD_{50}$ in mice. The test data below is for Meisoindigo 3.9 ±0.8 g/kg, and for NATURA 7.33±1.15 g/kg as compared to a value for Cisplatin of 15.9±1.3 mg/kg under the same experimental conditions.

It was found that at higher concentrations, Meisonindigo blocks tumor cells at G2+M phase at the second check point, allowing the targeting of those cancer cells that escape from treatments at the earlier stage of the cycle. At low concentrations, Meisoindigo inhibits cyclin-D mediated cdk activity, and at higher concentration, it interferes with both cyclin A and/or B mediated cdk activity and induces apoptosis (see FIG. 8).

Figure 2:
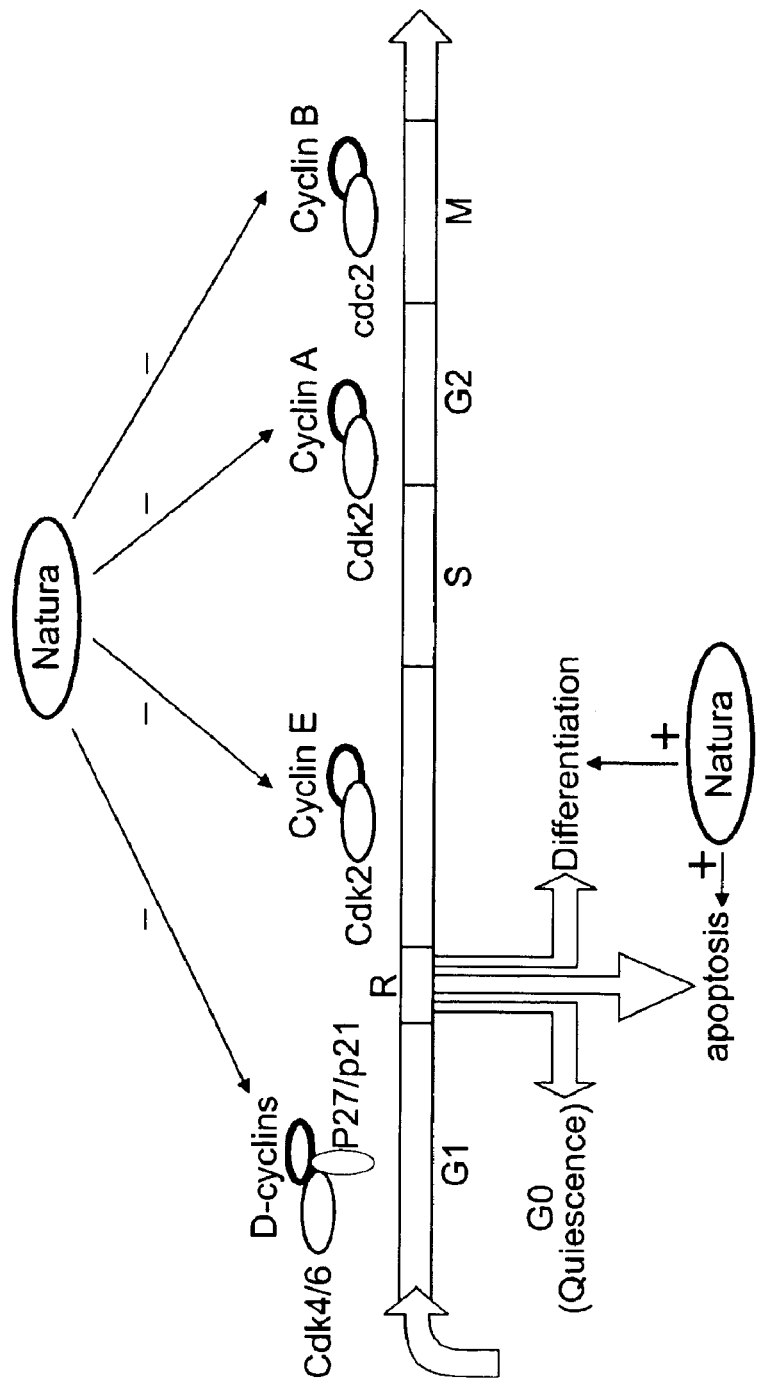
FIG. 2 shows a model of anticancer mechanisms of derivatives of isoindigo and indirubin.

FIG. 2 shows a model of anticancer mechanisms of NATURA. A typical cell cycle is classified into G1, S, G2 and M phases. R: the restriction point, at this point, cells can have different destinies: 1) To leave the cell cycle and enter a reversible quiescence phase, $G_0$, phase; 2) To exit cell cycle and undergo apoptosis; 3) To differentiate and irreversibly exit from the cell cycle, and 4) To pass through the restriction point and then become largely independent of extracellular signals and progress automatically through subsequent cell cycle phases (S, G2, M) to the next G1 phase. A variety of proteins are in turn responsible for the regulating progression of cells through the cell cycle. The key components of cell cycle machinery are the cyclins (D cyclins, cyclin A, cyclin B and cyclin E), the cyclin-dependent kinases (CDKs, cdk4/6, cdk2, and cdc2) and their inhibitors (p15/p16/p18/19, p21/p27). Meisoindigo and NATURA specifically inhibit activities of cdk4/6, cdk2, and cdc2, thus against cell proliferation. Those compounds have also showed to induce cell differentiation/maturation without affecting cell viability, and promoter apoptosis −: inhibits, and +: induce or promote the activity.

Example 1

Anticancer Activities of NATURA in Vitro By MTT

Growth inhibitory effects of NATURA and other agents on human cancer cells were determined by standard MTT (3-(4,5-dimethylthiazol-2-yl)-2,5-diphenyltetrazolium bromide Test) as described previously [16]. Briefly, cancer cells grown exponentially were aliquoted into 96-well plates at a density of 5000 cells/200 $\mu$l per well in RPMI 1640 medium containing 10% FBS overnight. The cells in the plates were then exposed to series of dilution of indicated agent. After 72 h of incubation, 100 $\mu$l of the medium was removed from each of the wells and 50 $\mu$l of a 1 mg/ml solution of 3-(4,5-dimethylthiazol-2-yl)-2,5-diphenyltetrazolium bromide (MTT) was added to each well and the cells were incubated for additional 4 h. 200 $\mu$l of solution of 0.04 N HCl-isopropanol was added to each well to dissolve the black fromazan participates, and absorbance at 540 nm was measured on a 96-Well.

Anticancer activity in animal models of Meisoindigo and NATURA: Two established animal cancer models, Lewis lung carcinoma, and Walker 256 sarcoma [17–20], have been used to evaluate anti-solid tumor activities of meisoindigo and NATURA as described previously. Briefly, C57 mice, body weight between 18 to 22 grams, and rat, body weight between 50 to 55 grams, were randomly divided into several groups, ten of each, respectively. Approximately $2 \times 10^6$ of Lewis cancer cells or Walker sarcoma cells were transplanted into mice or rat. Twenty-four hrs after the transplantation, equal molar dosages of indirubin, meisoindigo, NATURA or its sugar derivatives were given orally for 10 days. The animals in the control group were given 0.1 ml saline (drug vehicle, negative control) for the same periods of time as treated group. The animals at end of the treatment were sacrificed and tumors were removed and weighed.

Effects of NATURA on Human Cancer Cells: A good response of different types of human cancer cells to the treatment of Meisoindigo and NATURA was obtained by MTT after three day exposure, including cancer cell lines of breast (MCF-7 and SKBR-3, Table 1); colon (LOVO and DLD-1, Table 2), and hormone dependent and independent prostate (LNCaP, PC-3 and DU145, Table 3). As shown in Table 1–3, the growth inhibitory effects of Meisoindigo (IC50 2.15 to 8.31 $\mu$M) on all of those tested human cancer cell lines are much stronger than retinoid acid (IC50 21.45 to >50 μM), a differentiation inducer, and NS389 (IC50>200 μM), a new developed Cox 2 inhibitor. The anticancer activity of Based on IC50 of NATURA (IC50 from 1.64 to 6.92 μM), the anticancer activities of NATURA is slightly stronger than its parental compound Meisoindigo (IC50 2.1 to 8.3 μM). We expect that a much stronger anticancer activity of NATURA than Meisoindigo will occur in vivo due to a significant improvement of its bioavailability by increasing its solubility. Similar results for all of these tests were also obtained using SRB (sulforhodamine B, data not shown). The activities of NATURA against both hormone dependent and independent prostate cancers are also much stronger than that of clinical current hormone therapeutic agents, Casodex and Proscar (Table 3). No significant differences of those cancer cells in response to the treatment of Meisoindigo and NATURA were observed whereas cancer cells of breast and colon seem more sensitive than that of prostate (Table 3) in response to the treatment of Daunomycin. These data support that Meisoindigo and NATURA are against a common target of cancer cells, i.e. cyclin dependent kinases, thus it will be proven to be a useful chemotherapeutic agent for the treatment of various types of human solid tumors. Although the anticancer effect of Meisoindigo and NATURA are weaker than that of daunomycin or paclitaxel in vitro assay, it is noted that the toxicities of Meisoindigo and NATURA may much lower than those of agents as implicated by their LD50 (3.90±0.8 g/kg for Meisoindigo and 7.33±1.15 g/kg for NATURA in mice).

TABLE 1

Comparison of IC50 (μM) of Meisoindigo and NATURA with Chemotherapeutic Agents Against Breast Cancer Cell Lines by MTT

| Agent | CELL LINE | |
|---|---|---|
| | MCF-7 | SKBR-3 |
| Meisoindigo | 4.37 ± 0.31 | 2.17 ± 0.17 |
| NATURA | 2.91 ± 0.28 | 1.71 ± 0.14 |
| Daunomycin | 0.054 ± 0.011 | 0.061 ± 0.0051 |
| Retinoid | 21.45 ± 3.78 | >50 |
| NS389 | >200 | >200 |

TABLE 2

Comparison of IC50 (μM) of NATURA with Chemotherapeutic Agents Against Colon Cancer Cells by MTT

| Agent | CELL LINE | |
|---|---|---|
| | LOVO | DLD-1 |
| Meisoindigo | 5.76 ± 0.72 | 2.15 ± 0.17 |
| NATURA | 4.31 ± 0.59 | 1.64 ± 0.181 |
| Daunomycin | 0.035 ± 0.004 | 0.094 ± 0.0130 |
| Retinoid Acid | 75.34 ± 12.49 | 49.70 ± 5.72 |
| Paclitaxel | 0.00364 ± 0.00051 | 0.00315 ± 0.00037 |
| NS389 | >200 | >200 |

TABLE 3

Comparison of IC50 (μM) between Meisoindigo, NATURA and Chemotherapeutic Agents against Prostate Cancer Cell Lines.

| Agent | CELL LINE | | |
|---|---|---|---|
| | LNCaP | PC-3 | DU145 |
| Meisoindigo | 2.34 ± 0.33 | 3.26 ± 0.51 | 8.31 ± 0.93 |
| NATURA | 1.72 ± 0.27 | 2.41 ± 0.39 | 6.92 ± 0.73 |
| Daunomycin | N/A | 0.24 ± 0.018 | 0.107 ± 0.004 |
| Retinoid Acid | 15.95 ± 3.19 | >50 | >50 |
| NS389 | 65.54 ± 9.46 | >200 | >200 |
| Proscar | 40.60 ± 7.12 | 133.68 ± 12.94 | N/A |
| Casodex | 57.40 ± 7.21 | 120.11 ± 17.31 | N/A |

Figure 3:
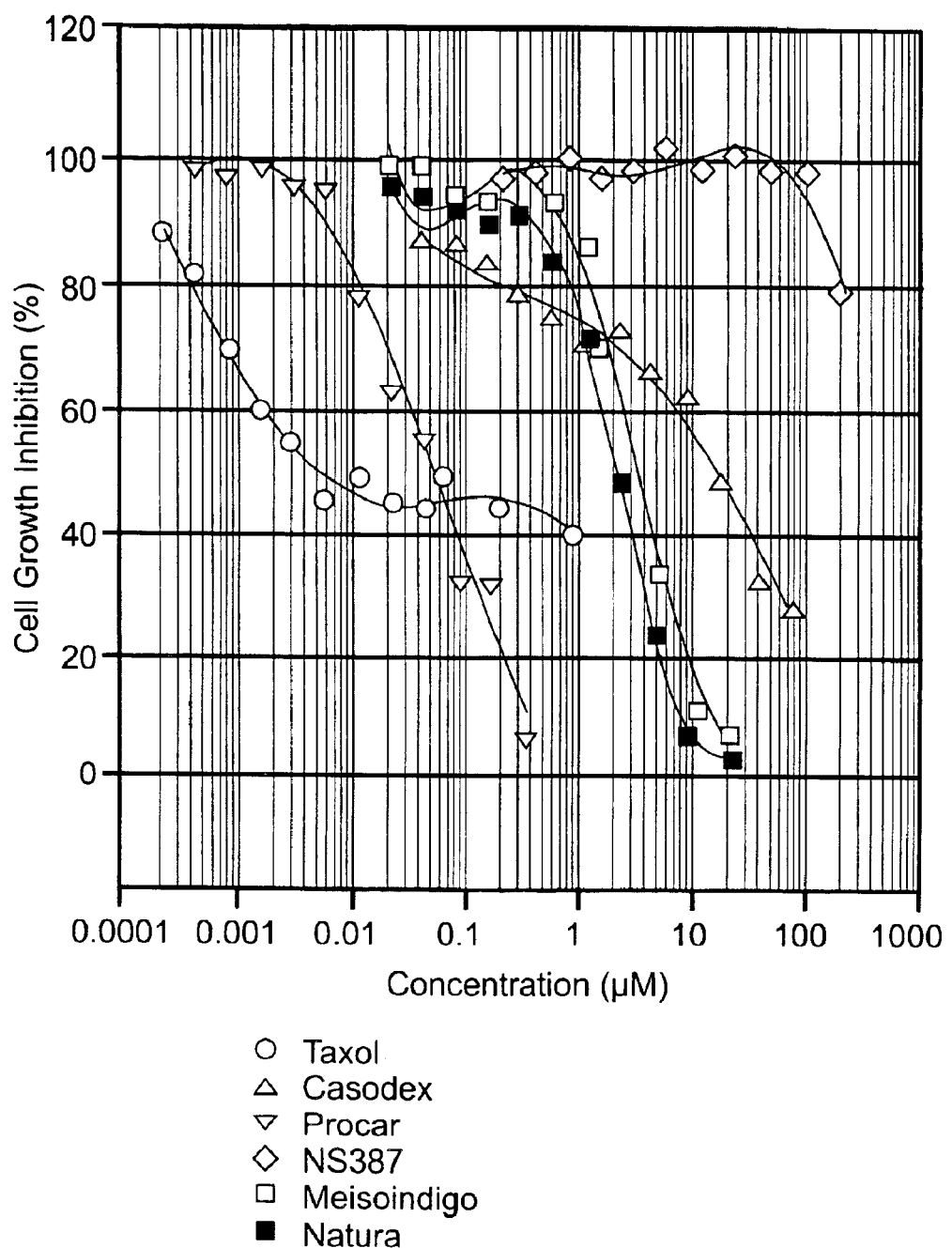
FIG. 3 is a graph of anticancer affects of NATURA in MCF-7 breast cancer cells.
Figure 4:
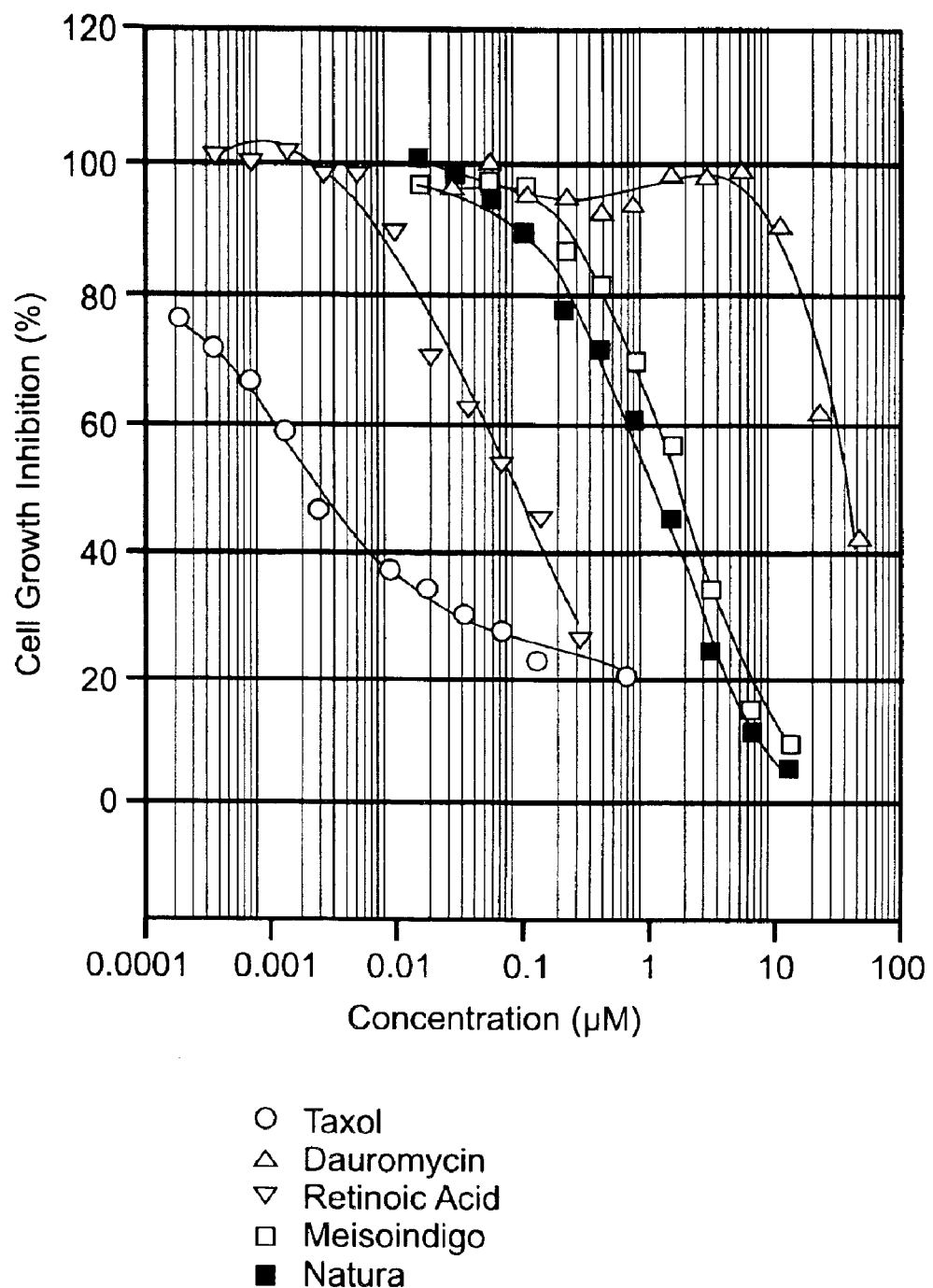
FIG. 4 is a graph of the anti-cancer activity of NATURA in DLD-1 colon cancer cells.
Figure 5:
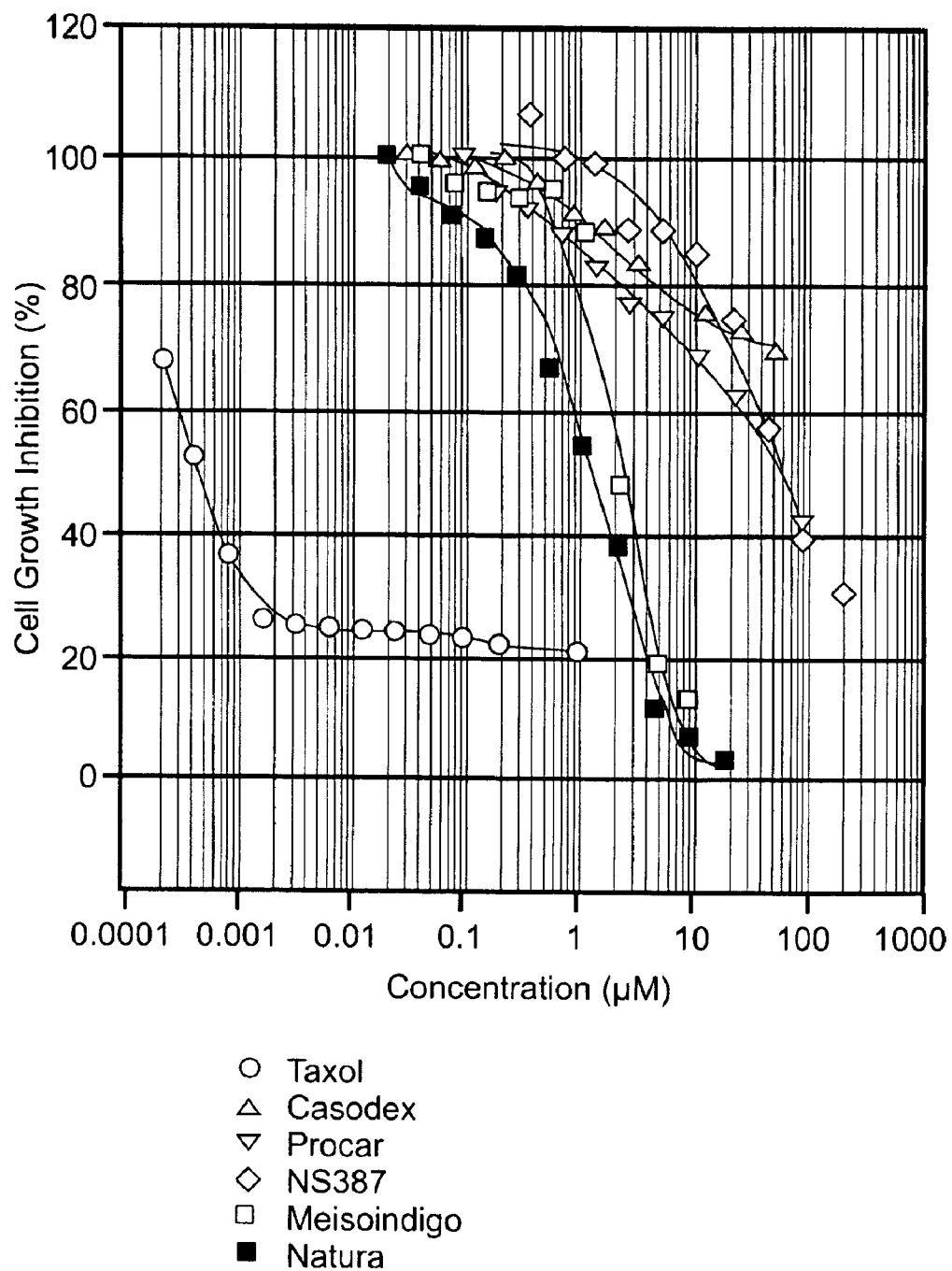
FIG. 5 is a graph of the anti-cancer activity of NATURA in LNCaP hormone-dependent prostate cancer cells.

FIGS. 3–5 show the anticancer affects of NATURA in MCF-7 breast cancer cells, DLD-1 colon cancer cells, and LNCaP hormone-dependent prostate cancer cells. The cancer cells grown exponentially were aliquoted into 96-well plates at a density of 5000 cells/200 μl per well in RPMI 1640 medium containing 10% fetal bovine serum (FBS) overnight. The cells in the plates were then exposed to series of dilution of indicated agent. After 72 h of incubation, 100 μl of the medium was removed from each of the wells and 50 μl of a 1 mg/ml solution of 3-(4,5-dimethylthiazol-2-yl)-2,5-diphenyltetrazolium bromide (MTT) was added to each well and the cells were incubated for additional 4 h. 200 μl of solution of 0.04 N HCl-isopropanol was added to each well to dissolve the black fromazan participates, and absorbance at 540 nm was measured on a 96-Well Microplate Reader [16]. Each experiment was repeated at least three times.

Figure 6:
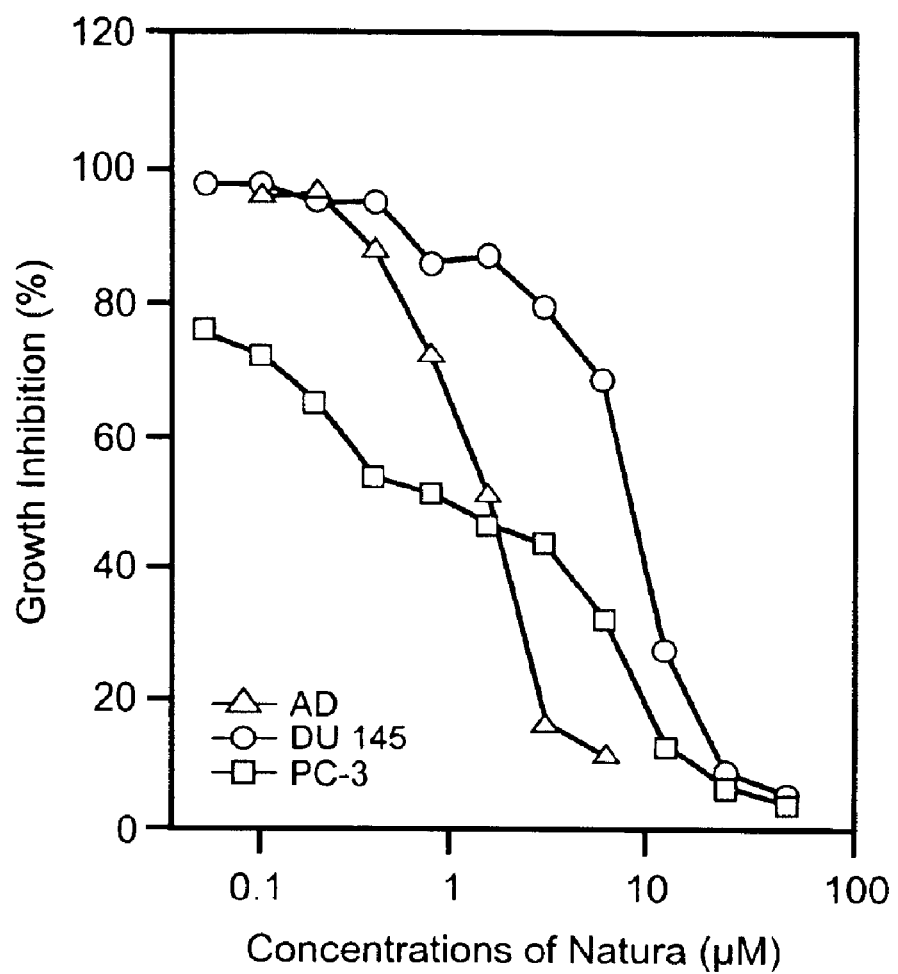
FIG. 6 is a graph of the effects of NATURA on hormone dependent and independent prostate cancer cell growth.

FIG. 6 shows the anticancer affects of NATURA in hormone dependent and independent prostate cancer cells. HUVEC and LNCaP cells were cultured in EMB (endothelial cell basal medium) and RPMI 1640 containing 10% FBS, respectively. The cells grown exponentially were exposed to indicated concentrations of meisoindigo or NATURA for 24 hr. The cells were harvested, washed, and total proteins extracted as described previously [13]. One hundred μg of the proteins were immuno-precipitated using antibodies against either cdk4/6 or cyclin D1 overnight at 4° C. in the presence of a cocktail of protease inhibitors. The immuno-precipitates were washed 4 times with protein extraction buffer and once with kinase assay buffer, and reacted with 75 μg/ml histone H1 in the presence of [γ-$^{32}$P]-ATP. The phosphorylated histone H1 (represent cdk activity) was measured by scintillation counting.

Figure 7:
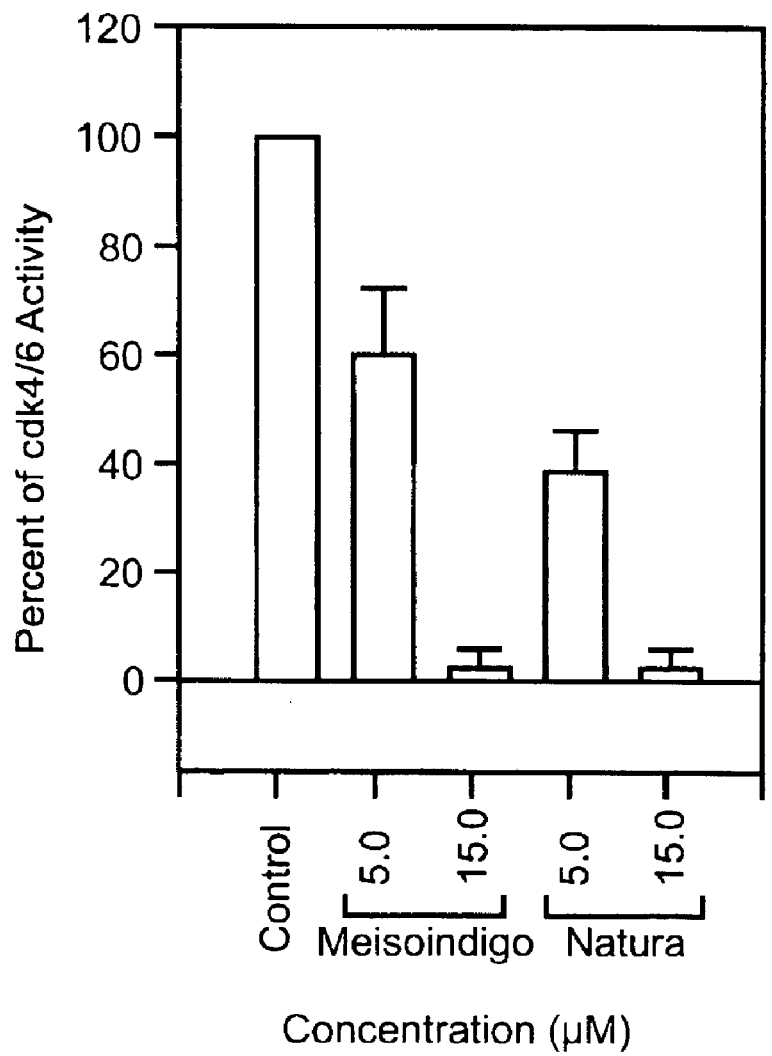
FIG. 7 is a graph of the inhibitory compound NATURA on cdk4/6 activity.

The inhibitory nature of NATURA and Meisoindigo on Ckd4/6 activity is shown in FIG. 7. Two different concentrations of 5.0 and 15.0 μm were used. The lower concentration of 5.0 μm of NATURA had a greater inhibitory affect on the cdk4/6 activity then did the same concentration of meisoinidgo. Smaller dosages of NATURA can be used to treat a subject having cancer making NATURA useful in small amounts, increasing the possibility of using NATURA in combination with other therapeutic drugs.

Figure 8:
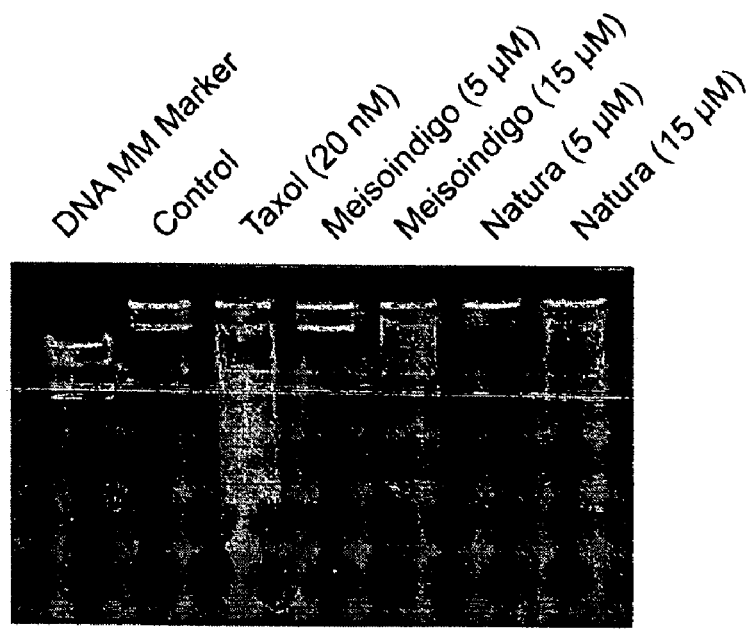
FIG. 8 shows the level of DNA fragmentation in prostate cancer LNCaP cells (panel A) and neuroblastoma N2A cells (panel B) having been exposed to Meisoindigo, NATURA or Taxol.
Figure 8:
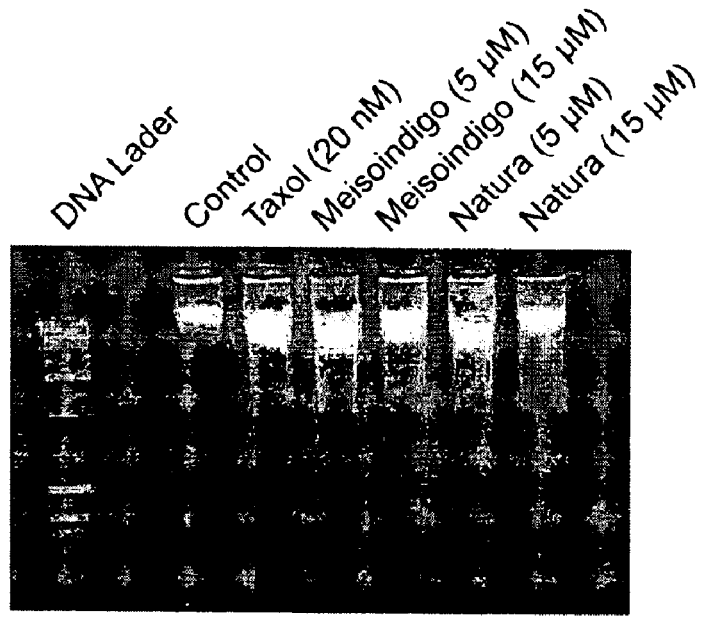

FIG. 8 shows the induction of DNA fragmentation in prostate cancer LNCaP cells (panel A) and neuroblastoma N2A cells (panel B) a sign of apoptosis. Once cancer cells have been arrested at G1 phase by either derivatives of the invention, such as, Meisiondigo or NATURA, they will either differentiate or enter apoptosis. Our studies have demonstrated that approximately 48% of ML-1 cells became differentiated morphologically 5 days after exposure to Meisoindigo or NATURA. We also observed some L1210 leukemia cells became apoptotic by flow cytometry (FCM), suggesting that Meisoindigo and NATURA have a capacity to induce cell apoptosis. FIG. 8 confirms that Meisoindigo and NATURA cause apoptosis. The formation of DNA fragmentation (ladder) were measured, an indicator of cell apoptosis, in both LNCaP prostate and N2A neuroblastoma cells. To do this LNCaP and neuroblastoma N2A cells at exponential growth phase were exposed to indicated concentrations of Meisoindigo or NATURA or Taxol (20 nM, as a positive control) for 2 days. The cells were harvested, washed and DNA extracted. Approximately 2 μg per lane of DNA were subjected to 2% agarose gel electrophoresis. As shown in FIG. 8, both Meisoindigo and NATURA induced a significant DNA fragmentation in LNCaP cells at concentration of 15 μM. This action was found more potent in N2 A neuroblastoma than in LNCaP cells where 5 μM of either Meisoindigo or NATURA was sufficient to significantly induce DNA ladders (panel B) which was consistent with MTT data, indicating that N2 A neuroblastoma cells are more sensitive to either Meisoindigo or NATURA.

Example 2

Anticancer Activity of Meisoindigo in Vivo

As shown in Table 4, Meisoindigo showed significant anticancer activities for both Lewis Lung cancer and Walker 256 sarcoma and the activities were much stronger than that of its parental compound indirubin.

HUVEC cells (data not shown), indicating that Meisoindigo may also have anti-angiogensis activity.

These analyses indicate that Meisoindigo is an attractive therapeutic agent against various types of human cancers as they specifically target cyclin dependent kinases. Meisoindigo has already showed strong anticancer activities in animals. The stable and simple chemical structure of Meisoindigo makes it easy to synthesize and administer. Moreover, it possesses new chemical structure that exhibits anticancer activity, which can be used as a chemotherapeutic agent alone or in combination with other conventional agents for the treatment of various types of cancer with enhanced results.

Example 3

Chemical Synthesis of Meisoindigo. NATURA and its Derivatives

To synthesis Meisoindigo, typically, add equal molar amount of 2-hydroxyindole (see structure below) and N-methyl-indolinyl-diketone, glacial acetic acid (2.0 L of glacial acetic acid for one molar of the reaction substances), and hydrochloric acid (concentrated, 6.67 ml of HCl for one molar of the reaction substances) into three-neck flask, heat to 70–80° C., stir for 2 h, cool to room temperature. Bulk brown crystal precipitates are then formed. Filter, and sequentially wash with glacial acetic acid, distilled water, and ethanol. Melt point is measured. It should be between 235–237° C.

The mother reaction solution is poured into $dH_2O$, and brick-like red crystal precipitates are formed. Wash with $dH_2O$ until neutral. Combine two part of the crystal product,

TABLE 4

Anti-cancer activities of Meisoindigo and NATURA in animals.

| Tumor | Group | Dose (mg/kgxd) | No. of animals | Tumor Size X ± SD | Inhibition (%) | Statistic (ST test) |
|---|---|---|---|---|---|---|
| Lewis Lung Cancer | Control | — | 10 | 3.5 ± 0.44 | 0 | |
| | Indirubin | 100 × 9 | 10 | 2.58 ± 0.21 | 26.3 ± 2.8 | P < 0.05 |
| | Meisoindigo | 106 × 9 | 10 | 1.80 ± 0.15 | 48.6 ± 4.1 | P < 0.01 |
| Walker 256 | Control | — | 10 | 9.7 ± 1.02 | 0 | |
| | Indirubin | 100 × 9 | 10 | 3.94 ± 0.71 | 59.4 ± 2.9 | P < 0.01 |
| | Meisoindigo | 106 × 9 | 10 | 2.10 ± 0.17 | 71.6 ± 3.1 | P < 0.01 |

Previous studies have shown that Meisoindigo induces ML-1 cell differentiation and maturation while suppresses the expression of oncogene c-myb, and arrests the cancer cells at G1 phase [11]. Recently study has been shown that myb activation is linked to the phosphorylation mediated by cyclin dependent kinases, and suppress of cyclin D and its kinase activity have been indicated to play a role induction of cell differentiation. In this preliminary observation, we further confirmed Meisoindigo strongly suppresses D cyclins mediated cdk4/6 activity (FIG. 2). Over 56% of the enzyme activity was inhibited by 5.0 μM and complete inhibition was achieved when LNCaP prostate cancer cells were exposed to 15 μM of Meisoindigo for 24 h. Similar results were also obtained in human epithelial cell line and re-crystallized with glacial acetic acid. Yield is approximately 63%, melt point is 236–237° C.

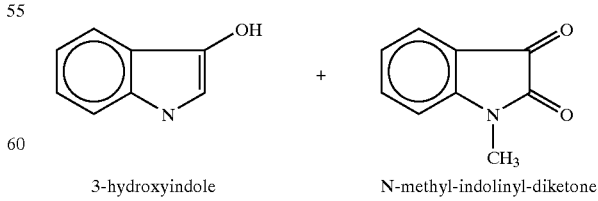

3-hydroxyindole          N-methyl-indolinyl-diketone

Also the method of chemical synthesis of NATURA and its derivatives compounds were synthesized using the following chemical path.

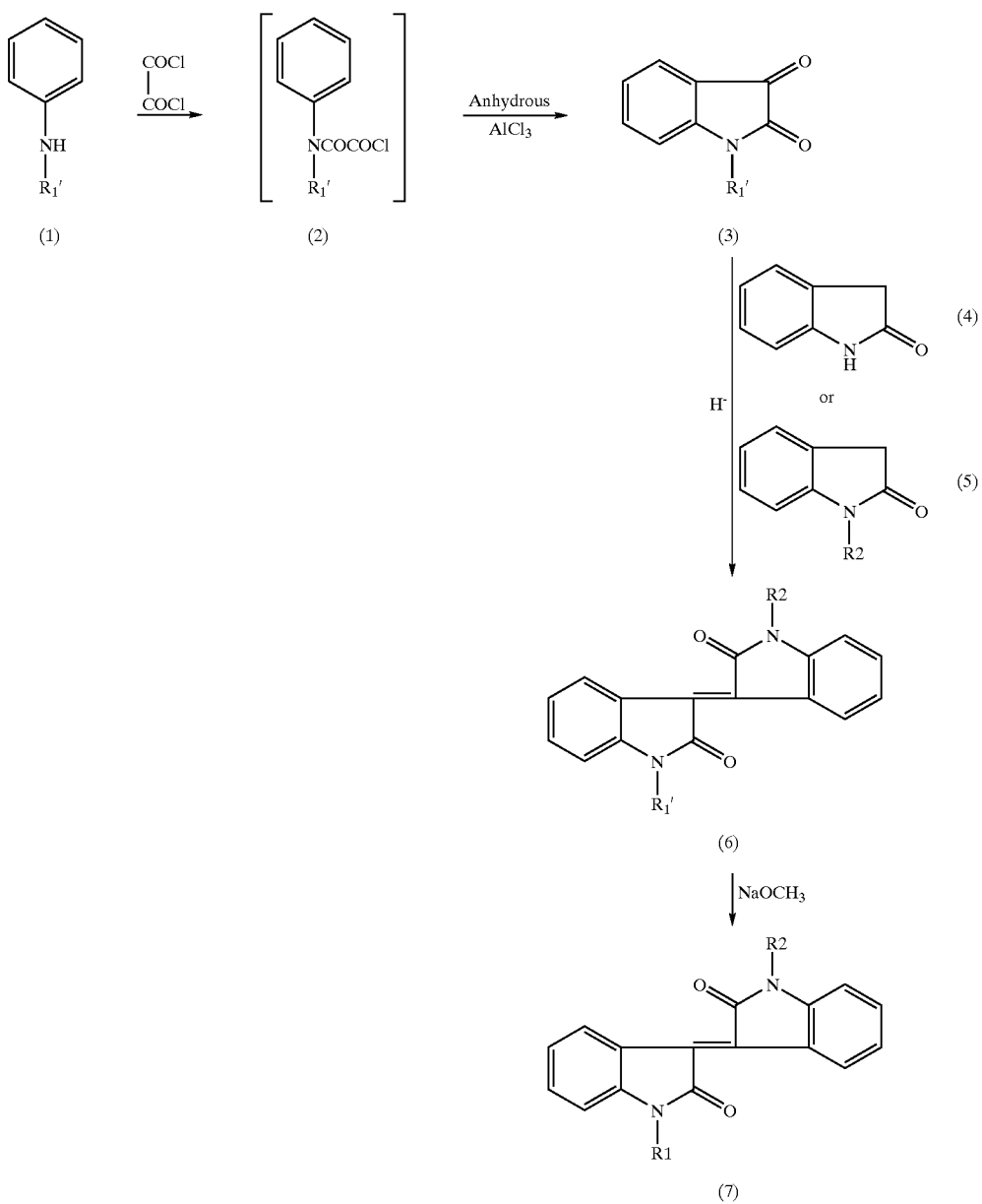

Compounds (1) (glycosides) were reacted with ClCO-COCl (oxaly chloride) in 95% alcohol solution to form intermediary Compounds 2 that became a stable Compounds 3 (isatin-glucosides) in the present of anhydrous $AlCl_3$. Where $R_1'$ represents sugar group of xylose, ribose, arabinose, glucose, or mannose. Compounds 3 were further reacted with 2-ketone indole (oxindole, Compound 4) or its derivatives Compounds 5 (R represents methyl- or ethyl-groups) in the presence of p-metyl-benzensulphonic acid to obtain Compounds 6. Acetyl-derivatives of Compounds 7 were finally obtained by reaction of Compounds 6 with $NaOCH_3$.

NATURA was synthesized using above method where $R_1'$ represented xylose-, $R_2$ hydrogen, and R1 1-(β-D-O-Triacetyl-xylopyranosyl)-. Bulk brown crystal precipitates of NATURA was filtered, and sequentially washed with glacial acetic acid, $dH_2O$, and ethanol. The compound was re-crystallized with glacial acetic acid and the chemical structure confirmed by spectrum of Mass, Infrared, and nuclear magnetic resonance. The yield was found to be approximately 63.8%.

The formula ($C_{28}H_{26}N_2O_9$) weight of NATURA, 1-(β-D-O-Triacetyl-xylopyranosyl)-isoindigo, is 534.52. It is a reddish crystal powder, no smell, and tasteless. It is soluble in dimethyl sulfoxide (DMSO), and slightly dissolves in ethanol, acetone, chloroform, and rarely dissolves in water.

Example 4

Synergistic Combinations of Meisoindigo

Effects of Meisoindigo in combinations with Casodex or Proscar or Casodex plus Proscar on prostate cancer cell growth were evaluated by MTT in LNCAP cells. A typical experiment was performed as follow: Exponential growing LNCAP cells were 96-well dished at density of 5,000 cells per well. Twenty-four hours after the incubation, the cells were exposed to series dilution of Meisoindigo, or Casodex or Proscar alone. For combinations, the cells were exposed to Meisoindigo with either Casodex or Proscar, or with Casodex plus Proscar at ratio of 1:10, 1:4 or 1:10:4, respectively. The maximal concentrations were 5 $\mu$M for Meisoindigo, 50 $\mu$M for Casodex, and 20 $\mu$M for Proscar, respectively. Three days after the incubation, the cell growth was measured by MTT as described in the EXAMPLE 1, the percentages inhibition were calculated, and data were analyzed by a PC program CalcuSyn of Biosoft edited by T.-C. Chou, Memorial Sloan-Kettering Cancer Center, New York, and Hayball, M. P. at Cambridge, UK, 1996 [24]. Combination index (CI) is used to evaluate the outcomes of a combination. If CI>1, the combination is antagonistic, CI=1, additive, and CI<1, synergistic. As shown in Table 5–7, the combinations of Meisoindigo either with Casodex or Proscar or Casodex plus Proscar resulted in significant synergistic anti-proliferation effects as indicated by their combination index (CI).

TABLE 5

Combination index (CI) of Meisoindigo and Casodex in LNCaP cells

| Meisoindigo ($\mu$M) | CASODEX ($\mu$M) | Percent of Inhibition | CI |
|---|---|---|---|
| 0.0098 | 0.0980 | 0.9580 | 0.454 |
| 0.0195 | 0.1950 | 0.8585 | 0.213 |
| 0.0390 | 0.3900 | 0.8000 | 0.275 |
| 0.0780 | 0.7800 | 0.5780 | 0.186 |
| 0.1560 | 1.5600 | 0.6320 | 0.466 |
| 0.3125 | 3.1250 | 0.5306 | 0.616 |
| 0.6250 | 6.2500 | 0.4750 | 0.990 |
| 1.2500 | 12.5000 | 0.3040 | 0.975 |
| 2.5000 | 25.0000 | 0.1200 | 0.644 |
| 5.0000 | 50.0000 | 0.0555 | 0.585 |

TABLE 6

Combination index (CI) of Meisoindigo and Proscar in LNCaP cells

| Meisoindigo ($\mu$M) | Proscar ($\mu$M) | Percent of Inhibition | CI |
|---|---|---|---|
| 0.0195 | 0.0780 | 0.919 | 4.555 |
| 0.0390 | 0.1560 | 0.900 | 5.243 |
| 0.0780 | 0.3120 | 0.814 | 1.908 |
| 0.1560 | 0.6240 | 0.633 | 0.449 |
| 0.3125 | 1.2500 | 0.572 | 0.510 |
| 0.6250 | 25.000 | 0.567 | 0.976 |
| 1.2500 | 5.0000 | 0.457 | 0.753 |
| 2.5000 | 10.0000 | 0.409 | 1.000 |
| 5.0000 | 20.0000 | 0.282 | 0.645 |

TABLE 7

Combination index (CI) of Meisoindigo and Casodex plus Proscar in LNCaP cells

| Meisoindigo ($\mu$M) | CASODEX ($\mu$M) | Proscar ($\mu$M) | Percent of Inhibition | CI |
|---|---|---|---|---|
| 0.0098 | 0.0980 | 0.03904 | 0.8940 | 1.228 |
| 0.0195 | 0.1950 | 0.0780 | 0.8600 | 1.214 |
| 0.0390 | 0.3900 | 0.1560 | 0.7000 | 0.350 |
| 0.0780 | 0.7800 | 0.3120 | 0.6570 | 0.498 |
| 0.1560 | 1.5600 | 0.6240 | 0.5150 | 0.403 |
| 0.3125 | 3.1250 | 1.2500 | 0.427 | 0.506 |
| 0.6250 | 6.2500 | 25.000 | 0.3420 | 0.658 |
| 1.2500 | 12.5000 | 5.0000 | 0.2700 | 0.902 |
| 2.5000 | 25.0000 | 10.0000 | 0.1570 | 0.892 |
| 5.0000 | 50.0000 | 20.0000 | 0.0600 | 0.636 |

Example 5

Toxicological Study of Meisoindigo

Acute Toxicity

Determination of Median Lethal Dose LD50 (the dose causes death of 50% of animals tested): Eighty Kuan Ming white mice with body weight between 18–22 g were randomly divided into 8 groups each with 10 animals. The animals were given Meisoindigo suspension orally at dosage of 0, 1.85, 2.60, 3.60, 5.10, 7.14, and 10.00 g/kg respectively. The animals were tested for two weeks, and the LD50 was measured using modified Bliss method as follows. The earliest death of animals was observed in 2 days after the administration in the group with the highest dose. The data were shown in Table 8.

TABLE 8

Summary of frequency of death after administration of Meisoindigo.

| Dose (g/kg) | Log Dose | DFP* | [DF]²P² | Unit of DF |
|---|---|---|---|---|
| 10.00 | 1.00 | 1.00 | 1.00 | 7.326 |
| 7.14 | 0.85 | 0.80 | 0.64 | 5.842 |
| 5.10 | 0.70 | 0.70 | 0.49 | 5.524 |
| 3.60 | 0.55 | 0.60 | 0.36 | 4.642 |
| 2.60 | 0.41 | 0.20 | 0.04 | 3.249 |
| 1.86 | 0.27 | 0 | 0 | 2.674 |

*: DF: Frequency of Death; ΣDFP: Sum of DFP = 3.30, and Sum [DF]²P² = 2.53

LD50 was calculated using following equation:

$$LD50 = \log^{-1}[Xm - i(\Sigma DFP - 0.5)]$$

Here, Xm is the maximal frequency of death, Xm=I in this case; i is the distance of group. It is determined by following equation, in this case r=1.4

$$i = \log 1/r = 0.146$$

Thus, $LD_{50}$ was obtained as 3.9±0.8 g/kg.

Sub-Acute- and Chronic-Toxicity a) Sub-Acute Toxicity in Rats:

Forty Westar rats with body weight between 60–70 g were randomly divided into 4 groups each with 10 animals, and orally given Meisoindigo daily at dosage of 0, 100, 200, and 400 mg/kg respectively for 30 days. Body weights of all tested animals were examined weekly. The animals were then sacrificed for the examination of biochemical function and pathological alterations of blood, hear, liver, spleen, lung, and kidney. A slight reduction of body weight increase was observed in the group of animals given 400 mg/kg of Meisoindigo. No differences between control and tested groups were observed in biochemical functions of blood, liver and kidney. Examination of histochemistry of heart, liver, spleen, lung and kidney showed that only a slightly cloudy swelling appeared in liver of some rats given highest dosage (400 mg/kg), and no other pathological alterations were observed in any other tissues or organs.

b) Sub-Acute Toxicity in Dogs:

Two dogs were initially tested for sub-acute toxicity of Meisoindigo. They were orally given 10 mg/kg daily for 3 months. Minor gastro intestinal irritations were observed occasionally. No biochemical changes of blood, liver, and kidney including blood glucose, $K^+$, $Na^+$, etc. were observed during the period of testing.

Since no major toxicities were found during the initial study, an additional 3 dogs were tested by orally giving them a higher dose (20 mg/kg). Among them, one dog was given 20 mg/kg for 46 days, and another 2 dogs given for 2 months. No abnormalities were observed in all tested parameters, but animal's experienced intestinal irritations at various degrees, such as anorexia, nausea, and vomiting as well as black-green stool. However, all of those symptoms disappeared after the termination of the treatment of Meisoindigo. Therefore, one dog was given an escalated dosage i.e., from 20 mg/kg to 40 mg/kg for additional 12 days after day 73, and no biochemical abnormalities were found except gastro-intestinal irritation mentioned above. Histochemical examinations were performed in the dogs administered the highest dose, and showed cellular edema, fatty degeneration, and scatter hyperplasia inflammation in liver tissues.

c) Chronic Toxicity in Dogs:

On the basis of above initial tests, the sub-acute toxicities of Meisoindigo were further examined in dogs. Twelve dogs were randomly divided into 3 groups each having equal numbers of males and females, and orally given Meisoindigo at doses of 0, 5, and 10 mg/kg daily, respectively, for 6 months. No significant differences between control and tested animals were found during this period in hemogram (red blood cells, white blood cells, platelets, hematocrit, average red blood cell volume, total serum proteins, and serum album), functions of liver (SGPT), kidney (BUN) and heart (ECG). All parameters tested, in all animals, including controls fluctuated within normal ranges. Only a few animals occasionally experienced minor gastro-intestinal irritations, such as anorexia.

Twenty-four hours after the termination of Meisoindigo, half of the animal of each group were sacrificed, and dissected for pathological examination. No abnormalities were observed histochemically in heart, liver, lung, kidney, stomach, gastro intestine, testis, ovary, and lymph node.

Special Toxicity a) Reverse Mutation: Reverse Mutation was Examined using the Ames Test.

Meisoindigo at concentrations of 2, 20, 50, 100 and 200 $\mu$g/dish (10 cm), metabolically activated (+S9) and inactivated (−S9), were tested in strains of TA97, TA98, TA100 and TA102 (amino acid deficit *salmonella typhimurium*) respectively. Daunomycin, 2-aminofluorene (2AF), methylmethanesulfonate (MMS), 2,7-2AF, and 2-hydroxyanthraquinone were used as positive controls. No induction of reverse mutations were observed at all tested groups of Meisoindigo, metabolically activated or non-activated, whereas all groups of positive controls showed significant increases in reverse-mutated colony formation.

b) Induction of Micronuclei in Rodent Animals:

Ten KM white mice were divided into 5 groups, and given orally Meisoindigo at dosage of 0, 0.4, 0.8 and 2.0 g/kg (equal to 1/10, 1/5, and 1/10 of LD50, respectively) daily for 2 days. Cyclophosphamine at dosage of 48 mg/kg was given intraperitoneally daily for 2 days as positive control. Six hrs after the latest administration, the animals were sacrificed, and polychromatic erythrocytes from bone marrow were stained with Giemsa to count micronuclei. No differences were obtained between negative control and Meisoindigo-tested groups (1.86, 1.33, and 2.66 per thousand for the tested groups compared with 1.33 per thousand of control group), whereas, micronuclei significantly increased in positive control (41.16 per thousand against negative control 1.33 per thousand). These data demonstrated a negative induction of micronuclei of Meisoindigo.

c) Aberration of Chromosome in Human Lymphocytes:

Human blood withdrawn from healthy males was cultured in the presence of metabolically activated, or non-activated different concentrations of Meisoindigo (0, 5, 10, and 25 $\mu$M) for 72 hrs, or aflatoxin B1 (AFB1) and mitomycin C (MMC) as positive controls. The aberration of chromosomes was then examined under microscope. No differences were found between negative controls and all Meisoindigo-tested groups, metabolically activated or non-activated, (P>0.05), whereas, the differences between positive and negative controls were significant (P<0.01).

Example 6

Anticancer Activities of NATURA and its Derivatives in Vivo:

Previous studies have shown that Meisoindigo induces ML-1 cell differentiation and maturation while suppresses the expression of oncogene c-myb, and arrests the cancer cells at G1 phase [11]. Recent studies show that myb activation is linked to the phosphorylation mediated by cyclin dependent kinases, and suppress of cyclin D and its kinase activity have been indicated to play a role induction of cell differentiation. In this preliminary observation, we confirmed that NATURA and its derivatives strongly suppresses D cyclins mediated cdk4/6 activity (FIG. 2, and 3). Over 56% of the enzyme activity was inhibited by 5.0 $\mu$M and complete inhibition was achieved when LNCaP prostate cancer cells were exposed to 15 $\mu$M of NATURA for 24 h. Similar results were also obtained in human epithelial cell line HUVEC cells (data not shown), indicating NATURA and its derivatives may also have anti-angiogensis activities.

These analyses indicate that NATURA and its derivatives are also attractive therapeutic agent againsts various types of human cancers as they specifically target cyclin dependent kinases. IC50 of NATURA for all tested human cancer cell lines was found to be between approximately 1.64 to 6.92 $\mu$M, an effective range as shown by many clinical therapeutic agents. The stable and simple chemical structure of NATURA makes it easy to synthesize and administer. Moreover, the new chemical structure of NATURA and its derivatives that exhibit anticancer activity, which can be used as a chemotherapeutic agent alone or in combination with other conventional agents for the treatment of various types of cancer with enhanced results.

For example, cancer patients undergoing chemotherapy often experience hair loss. Although temporary, this effect is emotionally distressing, a constant visual reminder of the individual's condition. Many anti-cancer drugs that lead to CIA target specific phases of the cell cycle. As a result, they prove selectively toxic to cells undergoing division. The epithelium of the hair follicle is particularly sensitive to these effects because it divides so rapidly. It is known that the inhibition of cell cycle progression diminishes the toxicity of the drugs. Accordingly, the combination of NATURA taken orally, at low dosage so that it has very low toxicity, would be beneficial in reducing the extent of hair loss in patients undergoing treatment for such situations. In addition, the amount of conventional chemotherapy agent would be reduced, in turn further reducing the extent of hair loss in the patient. Thus, the combination of NATURA with a conventional cancer treatment agent will result in similar treatment efficacies with fewer side effects than in conventional chemotherapy.

Comparison of Activities of NATURA and its Sugar Derivatives Against Walker 256

In order to assess the anticancer activities of NATURA and other sugar derivatives, Wistard rats transplanted with W256 were given the same molar of the tested compounds (0.384 mM/kg) for the same period of time (10 days). As shown in Table 9, NATURA (Xyl-Ac) exhibited best activity with 77% inhibition on the tumor. All derivatives contain only sugar group showed much weaker activity or no activity at all against W256 tumor, possibly because the molecules can't pass through cell membrane due to high polarity.

TABLE 9

Activity of NATURA and its derivatives against Walker 256

| R (substituted group) | Percent of Inhibition | P Value |
|---|---|---|
| Xyl-Ac*NATURA) | 77.5 | <0.001 |
| Xyl | 17.5 | >0.05 |
| Glu-Ac | 29.4 | <0.05 |
| Glu | No activity | N/A |
| Ara-Ac | 54.4 | <0.01 |
| Ara | No activity | N/A |
| Manno-Ac | N/A | N/A |
| Manno | N/A | N/A |
| Ribo-Ac | N/A | N/A |
| Ribo | N/A | N/A |

Xyl: xylose, Glu: gluose, Ara: arabinose, Manno: mannose, Ribo: ribose, Ac: triacetylated at the positions same as NATURA.

Inhibition of Mesioindigo and NATURA on cdk Activity

Figure 9:
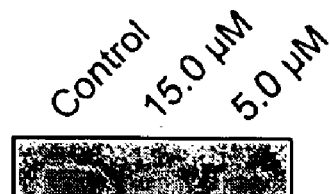
FIG. 9. shows the effects of Nature on cdk2 and cdk4 in an androgen dependent prostate cancer cell line LNCaP.
Figure 9:
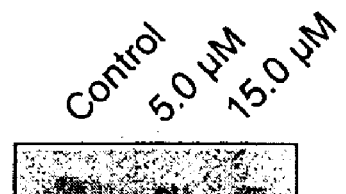
Figure 9:
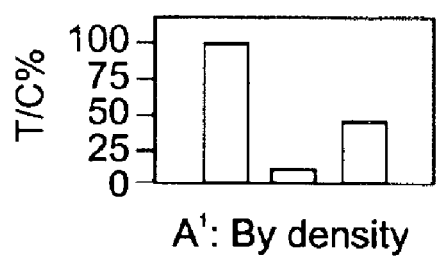
Figure 9:
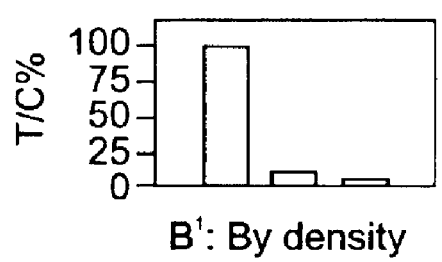

Our previous studies have showed that Meisoindigo induce ML-1 cell differentiation and maturation while suppressing the expression of oncogene c-myb, and arresting the cancer cells at G1 phase [11]. Recently study has been shown that myb activation is liked to the phosphorylation mediated by cyclin dependent kinases. In addition, suppressions of cyclin D and its kinase activity have been shown to play a role in the induction of cell differentiation [25–27]. We further confirmed Meisoindigo strongly suppress D cyclins mediated cdk4/6 activity. Similar to Meisoindigo, after 24 hours incubation with LNCaP prostate cancer cells, NATURA at 5.0 $\mu$M and 15 $\mu$M inhibited cdk2 enzyme activity by approximately 46% and 92%, respectively. A slight stronger activity on cdk4 was obtained at 5 $\mu$M of NATURA. One typical example of these assays is shown in FIG. 9, panel A&B. IC50 of NATURA on tested cdks (cdk 2, 4/6) from separated experiments was between 1.5 to 6.0 $\mu$M in LNCAP cells. No remarkable differences in the inhibitions of Meisoindigo and NATURA on those cdks were observed.

Similar results were also obtained in human epithelial cell line HUVEC cells (data not shown), indicating the Meisoindigo and NATURA may also have anti-angiogenesis activity.

Figure 10:
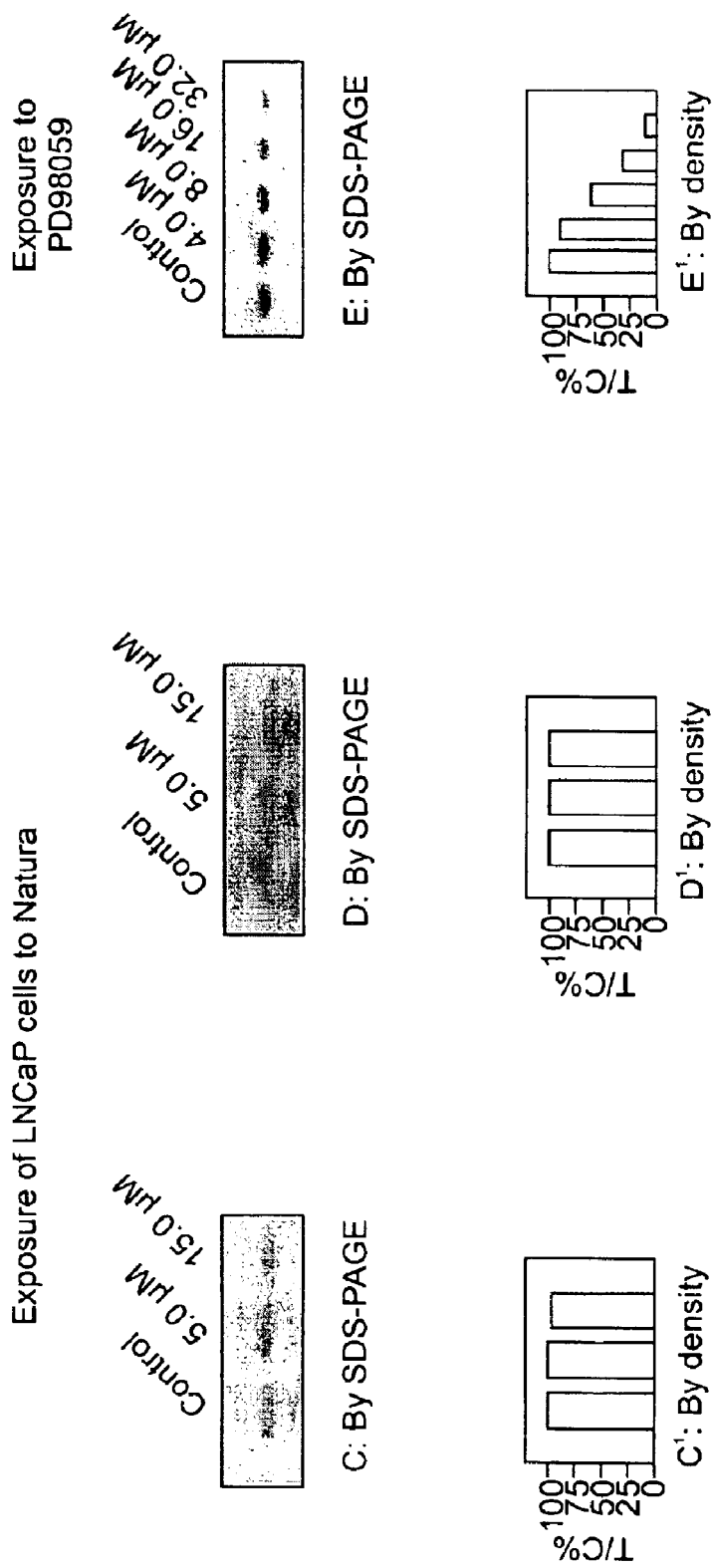
FIG. 10. shows the effects of NATURA on PKC and ERK1/2 activity in LNCaP cells.

The specificity of Meisoindigo and NATURA on cdk activities were further established by the examining the effects of those compounds on the activities of protein kinase C (PKC) and extracellular signal-regulated protein kinase 2 (ERK2, please note that the antibody was cross active to some extent against ERK1 as indicated by the supplier). One typical example is shown in FIG. 10, panels A&B. No inhibitory effect of NATURA on PKC and ERK2 activity was observed after treatment of LNCaP cells with as high as 15 $\mu$M of the agent for 24 hrs. This experiment was verified by treatment of the cells with a specific ERK inhibitor, PD98058 in the same cell line. Exposure of LNCaP cells to different concentrations of PD98058 for 15 min, a concentration-dependent inhibitory effects of PD98059 on ERK2 was observed as shown in FIG. 2, panel C, which was consistent with previous reports [28].

Figure 11:
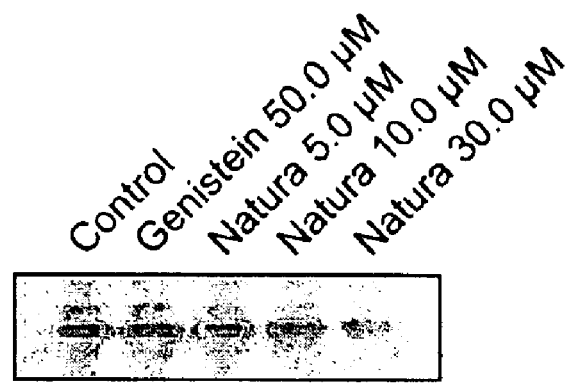
FIG. 11. shows direct inhibition of NATURA on immuno-purified cdk2 activity.
Figure 11:
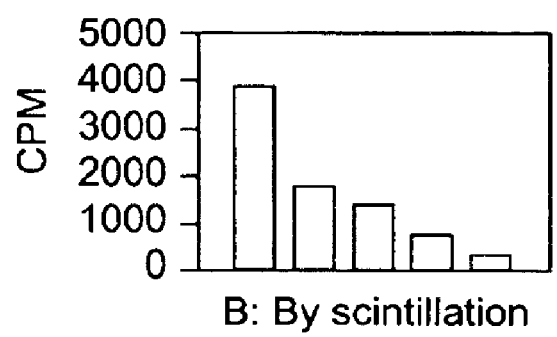

Direct inhibition of NATURAoncdk2 activity in vitro is shown in FIG. 11. When immuno-purified cdk2 from LNCaP cells was reacted with histone H1 in the presence of different concentrations of NATURA-$\beta$ and $\gamma$-[$^{32}$P]-ATP (2.5 $\mu$Ci/20 $\mu$M), the enzyme activity was decreased in a concentration-dependent manner. IC50 of NATURA for cdk2 was found to be 1.6±0.2 $\mu$M that paralleled the activity observed above. As a positive control, genistein at concentration of 50 $\mu$M achieved approximately 56% inhibition on cdk2 activity under the same experimental conditions, which is consistent with previous report [29].

ATP competing assays in vitro showed that 10 $\mu$M of NATURA achieved over 50% inhibitory effect on the immuno-purified cdk2 at ATP concentration as high as 100 $\mu$M, indicating that NATURA-$\beta$ has higher affinity than that of ATP to the enzyme.

Figure 12:
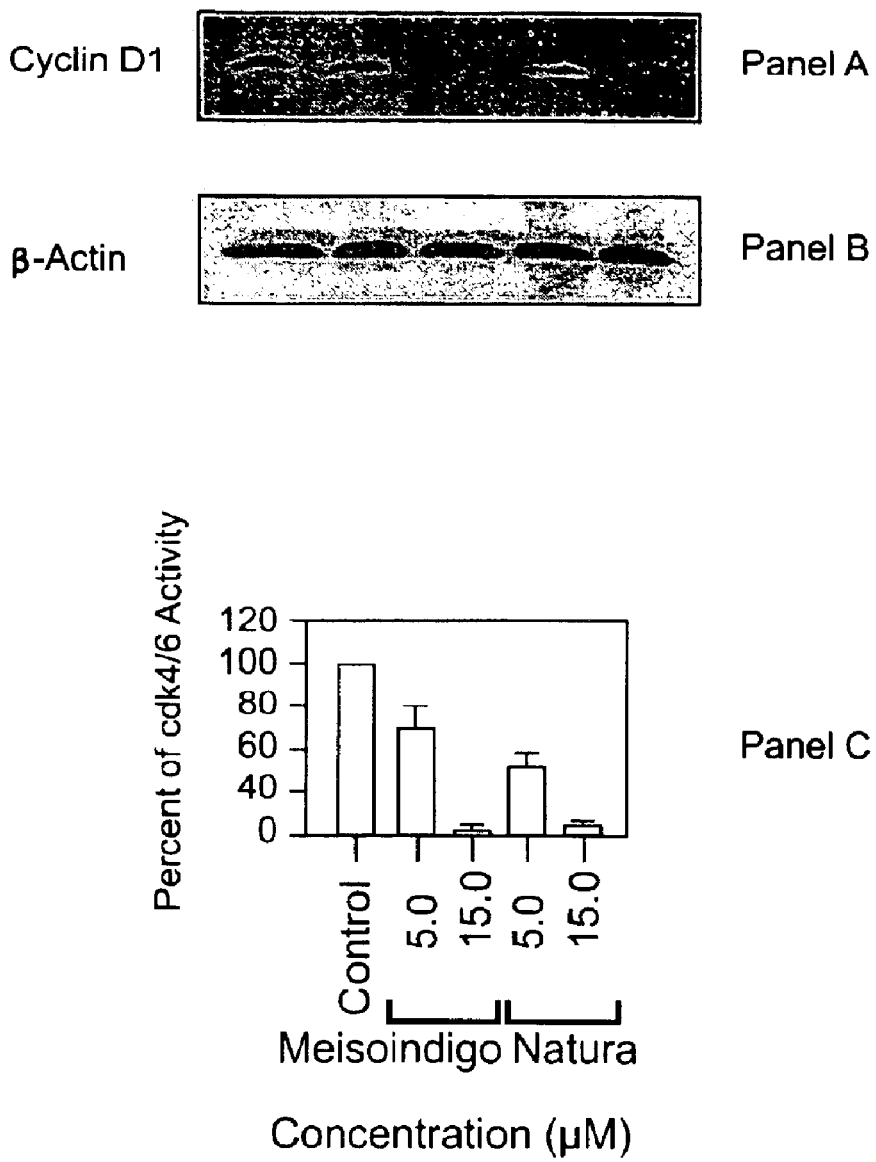
FIG. 12. shows the effect of Meisoindigo and NATURA on the protein level of cyclin D1.

Meisoindigo and NATURA also significant inhibit expression of cyclin D1 in HUVEC cells. Exponentially growing HUVEC cells were exposed to 5.0 and 15 $\mu$M of Meisoindigo and NATURA, 24 hrs after the exposures, the cells were harvested, washed, and total proteins extracted for Western blot analysis [13] using a monoclonal antibody specific against cyclin D1 (Dako). As shown in FIG. 12, both Meisoindigo and NATURA strongly inhibit expression of cyclin D1 in this cell lines. The cyclin D1 protein almost completely lost when the cells were exposed to 15 $\mu$M of either Meisoindigo and NATURA. As a result, phosphorylation of a tumor suppressor protein Rb, a native substrate of cyclin D1 mediated cdks, was diminished (data not shown).

Induction of Apoptosis: As we mentioned previously that cancer cells probably have two options after arrest at G1 phase, i.e. differentiation or apoptosis. Our previous studies have demonstrated that approximately 48% of ML-1 cells became differentiated morphologically 5 days after exposure to Meisoindigo. We also observed some L1210 leukemia cells became apoptotic by flow cytometry (FCM), suggesting Meisoindigo also have a capacity to induce cell apoptosis. To confirm our hypothesis and earlier observations, we measured poly(ADP-ribose) polymerase (PARP) degradation and the formation of DNA fragmentation (ladder), indicators of cell apoptosis [30, 31], in both LNCaP prostate and N2A neuroblastoma cells. LNCaP and neuroblastoma N2A cells at exponential growth phase were exposed to indicated concentrations of Meisoindigo or NATURA or Taxol (20 nM, as a positive control) for 2 days. The cells were harvested, washed and DNA extracted. Approximately 2 $\mu$g per lane of DNA were subjected to 2% agarose gel electrophoresis. As shown in FIG. 8, both Meisoindigo and NATURA induced a significant DNA fragmentation in LNCaP cells at concentration of 15 $\mu$M. This action was found more potent in N2 A neuroblastoma cells where 5 $\mu$M of either Meisoindigo or NATURA was sufficient to significantly induce DNA ladders (panel B) which was consistent with MTT data, indicating that N2 A neuroblastoma cells are more sensitive to either Meisoindigo and NATURA.

Figure 13:
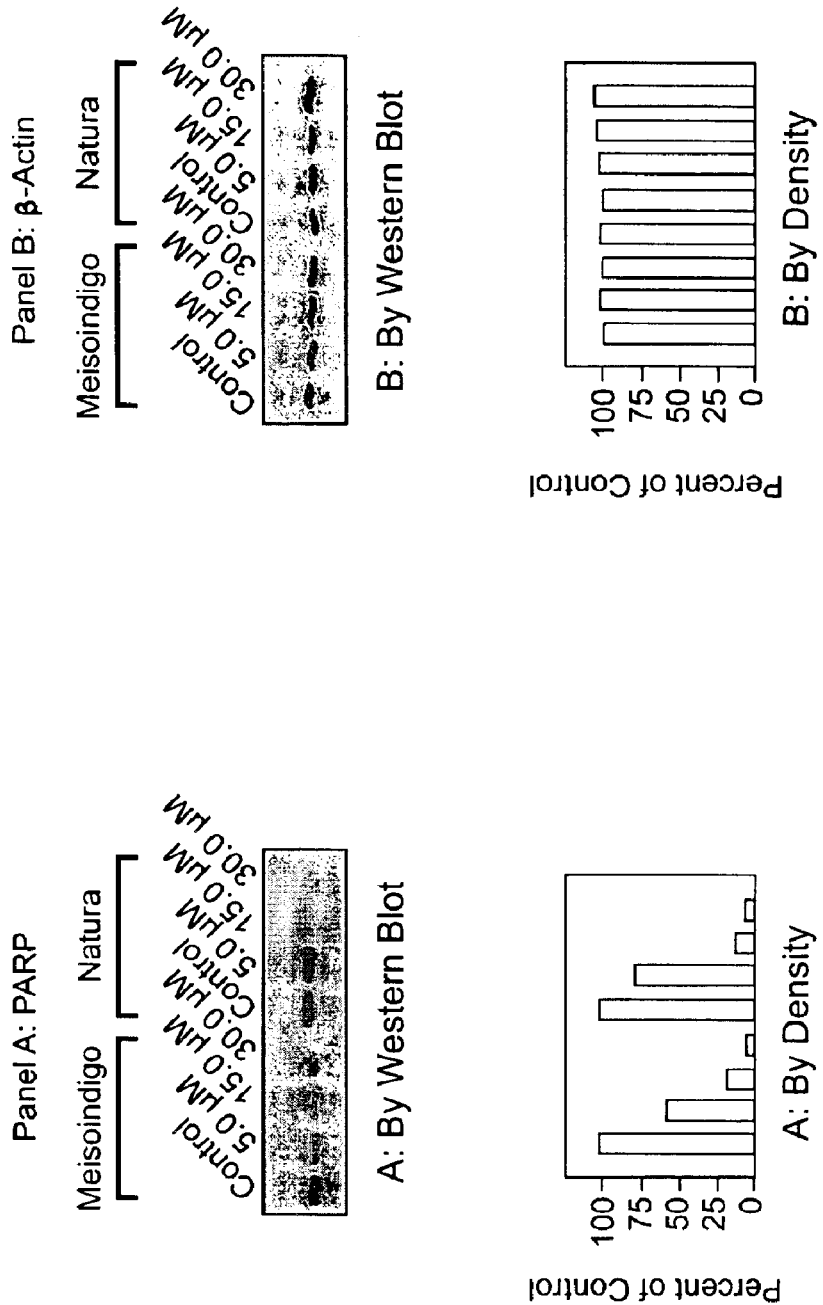
FIG. 13. shows the degradation of poly(ADP-ribose) polymerase in neuroplastoma N2A cells.

Consistent with the DNA ladder formation, a strong induction of PARP protein degradation was observed when N2A cells were exposed to either Meisoindigo or NATURA (FIG. 13). Our data thus, demonstrate that both Meisoindigo and NATURA significantly induce human cancer cell apoptosis.

Comparison of Activities of NATURA and its Derivatives:

TABLE 10

IC50 of NATURA and its derivatives in LNCaP cells

| $R_1$ or $R_2$ (substituted group) | IC50 ($\mu$M) |
|---|---|
| Xyl-Ac* (NATURA) | 1.72 |
| Xyl | 17.5 |
| Glu-Ac | 2.38 |
| Glu | >20.0 |
| Ara-Ac | 2.1 |
| Ara | >20.0 |
| Manno-Ac | 2.52 |
| Manno | >20.0 |
| Ribo-Ac | 1.62 |
| Ribo | 18.9 |

Xyl: xylose, Glu: gluose, Ara: arabinose, Manno: mannose, Ribo: ribose,
Ac: triacetylated at the positions same as NATURA.

All derivatives containing an unacetylated sugar group showed much weaker activity against LNCaP cells, possibly because the molecules had a low membrane diffusion capacity due to high polarity. Whether or not a small molecule can pass through cell membrane is determined by its ratio of o/w (oil/water). If polarity is too high (water soluble) or too low (oil soluble), the molecule will be difficult to pass the membrane through simple diffusion. The inventors surprisingly found that acetylations (triacetylated group) reduce polarity of the sugar-isoindigo molecule to a suitable o/w ratio increasing membrane diffusion capacity and bioavailability.

FIG. 9. shows the effects of Nature on cdk2 and cdk4 in an androgen dependent prostate cancer cell line LNCaP. LNCaP cells grown exponentially were exposed to different concentrations of NATURA for 24 hrs. The cells were harvested, washed, and total proteins extracted for assays of cdk activities as described in the Materials and Methods. The upper panels (A & B) are imagines of the films from SDS-PAGE, and lower panels represent the density measured by an Imagine Densitometer from the same films (expressed as percent of control).

FIG. 10. shows the effects of NATURA on PKC and ERK1/2 activity in LNCAP cells. LNCaP cells at exponential growth phase were exposed to different concentrations of NATURA (panel A & B) for 24 hrs, or to PD98059 (panel C) for 15 min. The cells were harvested, washed, and total proteins extracted. One hundred mg of the protein extracts were immunoprecipiated with antibody against PCK (panel A), and ERK1/2 (panel B & C) overnight for kinase assays as described in the "Materials and Methods". Upper panels are the imagines of x-ray films from SDS-PAGE, and lower panels represent the densities of each band from the films determined by an Imagine Densitometer from the same films (expressed as the percent of control).

FIG. 11. shows direct inhibition of NATURA on immuno-purified cdk2 activity. Two hundred mg of total protein extracts were immuno-precipitated with cdk2 antibody overnight at 4° C. After 4 washes with PBSTDS, and once with kinase assay buffer, the immuno-purified enzyme was then reacted for 10 min with 10 mg of histone H1 in the presence of different concentrations of NATURA or 50 mM of genistein (as a positive control) and $\gamma$-[$^{32}$P]-ATP (2.5 mCi/10 mM). The phosphorylated histone H1 (reflecting cdk2 activity) was detected either by SDS-PAGE (upper panel), or radioactive scintillation counting (lower panel, after eliminating free $\gamma$-[$^{32}$P]-ATP).

FIG. 12. shows the effect of Meisoindigo and NATURA on the protein level of cyclin D1. HUVEC cells grown exponentially were treated for 24 hrs with 5 and 15 mM of Meisoindigo and NATURA. The cells were harvested, washed, and total proteins extracted for Western blot analysis as previously described [1] using antibodies specifically against cyclin D1 (panel A), and b-actin (equal loading control, panel B), and detected by ECL detection kit (Amersham). The levels of cyclin D1 from Panel A were quantitated by an imagine densitometor and normalized by b-action (Panel C).

FIG. 13. shows the degradation of poly(ADP-ribose) polymerase in neuroplastoma N2A cells. N2A cells grown exponentially were treated with different concentrations of Meisoindigo or NATURA for 24 hours. The cells were harvested, washed, and total proteins extracted for determination of PARP degradation by Western blotting as described previously [1]. Upper panels (A & B) are imagines from ECL films, and lower panels (A' & B') are densities of the corresponding bands measured by an Imagine Densitometer (expressed as the percent of control).

REFERENCES

1. Morgan, D. O., *Principles of CDK regulation*. Nature, 1995. 374(6518): p. 131–4.
2. Buolamwini, J. K., *Cell cycle molecular targets in novel anticancer drug discovery*. Curr Pharm Des, 2000. 6(4): p. 379–92.
3. Senderowicz, A. M., *Development of cyclin-dependent kinase modulators as novel therapeutic approachesfor hematological malignancies*. Leukemia, 2001. 15(1): p. 1–9.
4. Buchdunger, E., A. Matter, and B. J. Druker, *Bcr-Abl inhibition as a modality of CML therapeutics*. Biochim Biophys Acta, 2001. 1551(1): p. M11–8.
5. Druker, B. J., et al., *Activity of a specific inhibitor of the BCR-ABL tyrosine kinase in the blast crisis of chronic myeloid leukemia and acute lymphoblastic leukemia with the Philadelphia chromosome*. N Engl J Med, 2001. 344(14): p. 1038–42.
6. Han, J., *Traditional Chinese medicine and the search for new antineoplastic drugs*. J Ethnopharmacol, 1988. 24(1): p. 1–17.
7. DiPaola, R. S., et al., *Clinical and biologic activity of an estrogenic herbal combination (PC-SPES) in prostate cancer*. N Engl J Med, 1998. 339(12): p. 785–91.
8. Li, X. K., et al., *Huanglian, A chinese herbal extract, inhibits cell growth by suppressing the expression of cyclin B1and inhibiting CDC2 kinase activity in human cancer cells*. Mol Pharmacol, 2000. 58(6): p. 1287–93.
9. Damiens, E., et al., *Anti-mitotic properties of indirubin-3'-monoxime, a CDK/GSK-3 inhibitor: induction of endoreplication following prophase arrest*. Oncogene, 2001. 20(29): p. 3786–97.
10. Ji, X. J., et al., *Pharmacological studies of meisoindigo: absorption and mechanism of action*. Biomed Environ Sci, 1991. 4(3): p. 332–7.
11. Liu, X. M., et al., *Induction of differentiation and down-regulation of c-myb gene expression in ML-1 human myeloblastic leukemia cells by the clinically effective anti-leukemia agent meisoindigo*. Biochem Pharmacol, 1996. 51(11): p. 1545–51.
12. Marko, D., et al., *Inhibition of cyclin-dependent kinase 1 (CDK1) by indirubin derivatives in human tumour cells*. Br J Cancer, 2001. 84(2): p. 283–9.
13. Wang, L. G., et al., *Down-regulation ofprostate-specific antigen expression by finasteride through inhibition of complex formation between androgen receptor and steroid receptor-binding consensus in the promoter of the PSA gene in LNCaP cells*. Cancer Res, 1997. 57(4): p. 714–9.

14. Wang, L. G., et al., *Activation of casein kinase II in ML-1human myeloblastic leukemia cells requires IGF-1 and transferrin.* J Leukoc Biol, 1995. 57(2): p. 332–4.
15. Kong, M., et al., *Cyclin F regulates the nuclear localization of cyclin B1 through a cyclin-cyclin interaction.* Embo J, 2000. 19(6): p. 1378–88.
16. Kreis, W., D. R. Budman, and A. Calabro, *Unique synergism or antagonism of combinations of chemotherapeutic and hormonal agents in human prostate cancer cell lines.* Br J Urol, 1997. 79(2): p. 196–202.
17. Yamaura, T., et al., *Model for mediastinal lymph node metastasis produced by orthotopic intrapulmonary implantation of lung cancer cells in mice.* Hum Cell, 1999. 12(4): p. 197–204.
18. Mitani, N., et al., *Inhibitory effect of berberine on the mediastinal lymph node metastasis produced by orthotopic implantation of Lewis lung carcinoma.* Cancer Lett, 2001. 165(1): p. 35–42.
19. Freitas, J. J., et al., *Walker-256 tumor growth causes oxidative stress in rat brain.* J Neurochem, 2001. 77(2): p. 655–63.
20. Wicki, A. and V. Niggli, *The Rho/Rho-kinase and the phosphatidylinositol 3-kinase pathways are essential for spontaneous locomotion of Walker 256 carcinosarcoma cells.* Int J Cancer, 2001. 91(6): p. 763–71.
21. Gianni, L., et al., *Nonlinear pharmacokinetics and metabolism of paclitaxel and its pharmacokinetic/pharmacodynamic relationships in humans.* J Clin Oncol, 1995. 13(1): p. 180–90.
22. Ohtsu, T., et al., *Clinical pharmacokinetics and pharmacodynamics of paclitaxel: a 3-hour infusion versus a 24-hour infusion.* Clin Cancer Res, 1995. 1(6): p. 599–606.
23. Huizing, M. T., et al., *Pharmacokinetics of paclitaxel and metabolites in a randomized comparative study in platinum-pretreated ovarian cancer patients.* J Clin Oncol, 1993. 11(11): p. 2127–35.
24. Kreis, W., D. R. Budman, and A. Calabro, *Unique synergism or antagonism of combinations of chemotherapeutic and hormonal agents in human prostate cancer cell lines.* Br J Urol, 1997. 79(2): p. 196–202.
25. Steinman, R. A., *Cell cycle regulators and hematopoiesis.* Oncogene, 2002. 21(21): p. 3403–13.
26. Sharifi, N. and R. A. Steinman, *Targeted chemotherapy: chronic myelogenous leukemia as a model.* J Mol Med, 2002. 80(4): p. 219–32.
27. Furukawa, Y., *Cell cycle control genes and hematopoietic cell differentiation.* Leuk Lymphoma, 2002. 43(2): p. 225–31.
28. Alessi, D. R., et al., *PD 098059 is a specific inhibitor of the activation of mitogen-activated protein kinase kinase in vitro and in vivo.* J Biol Chem, 1995. 270(46): p. 27489–94.
29. Frey, R. S., J. Li, and K. W. Singletary, *Effects of genistein on cell proliferation and cell cycle arrest in normeoplastic human mammary epithelial cells: involvement of Cdc2, p21(waf/cip1), p27(kip1), and Cdc25C expression.* Biochem Pharmacol, 2001. 61(8): p. 979–89.
30. Boehrer, S., et al., *In lymphatic cells par-4 sensitizes to apoptosis by down-regulating bcl-2 and promoting disruption of mitochondrial membrane potential and caspase activation.* Cancer Res, 2002. 62(6): p. 1768–75.
31. Wu-Wong, J. R., et al., *Identification and characterization of A-105972, an antineoplastic agent.* Cancer Res, 2001. 61(4): p. 1486–92.

What is claimed is:
1. A compound of formula (I), (II), or (III)

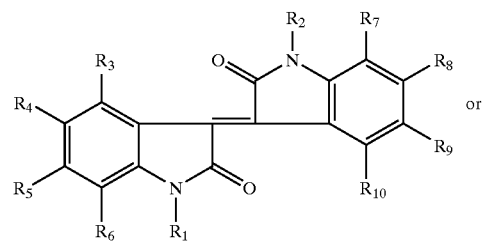

FORMULA (I)

or

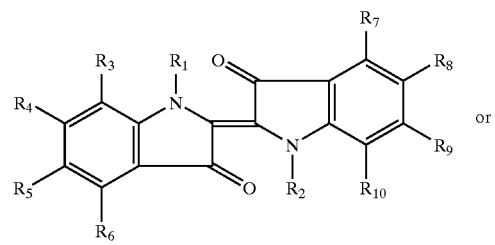

FORMULA II or

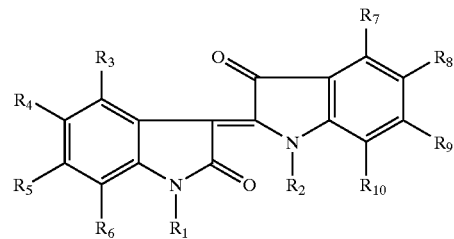

FORMULA (III)

wherein $R_1$ or $R_2$ is independently an acetylated monosaccharide; and $R_1$, $R_2$, $R_3$, $R_4$, $R_5$, $R_6$, $R_7$, $R_8$, $R_9$, or $R_{10}$ is independently a hydrogen, a monosaccharide, a disaccharide, a halogen, a hydrocarbyl group, or a functional hydrocarbyl group substituted with one or more hydroxy moieties, carboxy moieties, nitroxy moieties, monosaccharides, disaccharides, amines, amides, thiols, sulfate, sulfonate, sulfonamide, or halogens, wherein the hydrocarbyl has 1 to 12 carbon atoms.

2. The compound of claim 1, wherein $R_1$ or $R_2$, is an acetylated arabinose, glucose, mannose, ribose or xylose.

3. A pharmaceutical composition for treatment of cancer in an animal, comprising a therapeutically effective amount of the compound of claim 1 and a pharmaceutically acceptable carrier.

4. The pharmaceutical composition of claim 1, comprising an additional agent selected from the group consisting of radiotherapeutic agents, hormonal therapy agents, immunotherapeutic agents, chemotherapeutic agents, cryotherapeutic agents and gene therapy agents.

5. The pharmaceutical composition of claim 1, wherein the compound is formulated for oral administration.

6. A method for treatment of cancer, comprising administering a therapeutically effective amount of the pharmaceutical composition of claim 3 to an animal.

7. The method of claim 6, wherein said animal is a human, and wherein the compound is administered in combination with an additional agent selected from the group consisting of radiotherapeutic agents, hormonal therapy agents, immunotherapeutic agents, chemotherapeutic agents, cryotherapeutic agents and gene therapy agents.

8. A method of synthesizing a meisoindigo compound comprising:
adding about equal molar amounts of 2-hydroxyindole and N-methyl-indolinyl-diketone to produce a reaction substance;
mixing the reaction substance with an excess amount of glacial acetic acid to make a mixture;
heating the mixture to about 70 to 80° C. for 1 to 3 hours to form a precipitate; and
recovering the precipitate as the meisoindigo compound.

9. The method of claim 8, wherein the precipitate is washed with at least glacial acetic acid, water, or ethanol.

10. A method of treating cancer in an animal, comprising administering to an animal with cancer a therapeutically effective amount of a compound of formula (I), (II), or (III)

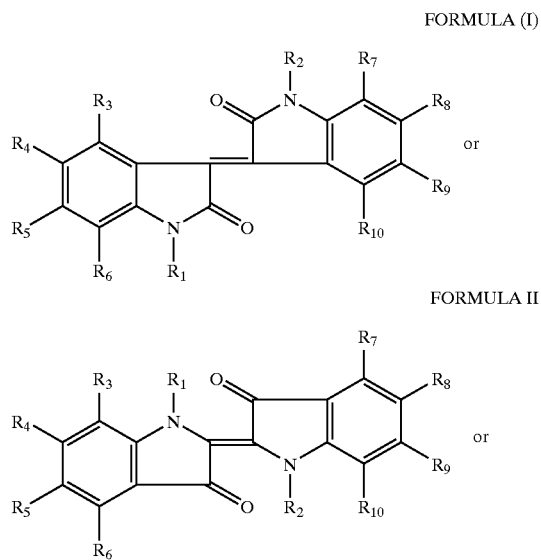

FORMULA (I)

or

FORMULA II or

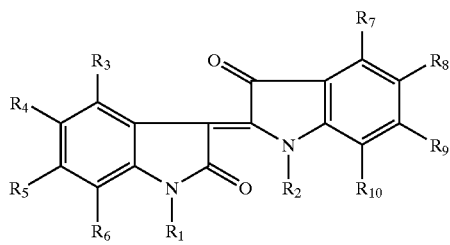

FORMULA (III)

wherein $R_1$ or $R_2$ is independently an acetylated monosaccharide; and $R_1, R_2, R_3, R_4, R_5, R_6, R_7, R_8, R_9,$ or $R_{10}$ is independently a hydrogen, a monosaccharide, a disaccharide, a halogen, a hydrocarbyl group, or a functional hydrocarbyl group substituted with one or more hydroxy moieties, carboxy moieties, nitroxy moieties, monosaccharides, disaccharides, amines, amides, thiols, sulfate, sulfonate, sulfonamide, or halogens, wherein the hydrocarbyl has 1 to 12 carbon atoms.

11. The method of claim 10, wherein $R_1$ or $R_2$, is an acetylated arabinose, glucose, mannose, ribose or xylose.

12. The method of claim 10, wherein said animal is a human and the composition is administered orally.

13. The method of claim 10, wherein the compound is administered in combination with an additional agent selected from the group consisting of radiotherapeutic agents, hormonal therapy agents, immunotherapeutic agents, chemotherapeutic agents, cryotherapeutic agents and gene therapy agents.

14. The method of claim 10, wherein the solid tumor cancer being treated is colon cancer, hormone dependent or independent prostate cancer, breast cancer, or lung cancer.

15. The method of claim 10, wherein the solid tumor cancer is hormone dependent or independent prostate cancer.

* * * * *